US009005964B2

(12) United States Patent
Verfaillie et al.

(10) Patent No.: US 9,005,964 B2
(45) Date of Patent: Apr. 14, 2015

(54) ENDODERMAL PROGENITOR CELLS

(75) Inventors: Catherine Verfaillie, Leuven (BE);
Lucas Chase, Madison, WI (US)

(73) Assignee: Regents of the University of Minnesota, St. Paul, MN (US)

( * ) Notice: Subject to any disclaimer, the term of this patent is extended or adjusted under 35 U.S.C. 154(b) by 1079 days.

(21) Appl. No.: 12/312,731

(22) PCT Filed: Nov. 26, 2007

(86) PCT No.: PCT/US2007/024415
§ 371 (c)(1),
(2), (4) Date: Feb. 9, 2010

(87) PCT Pub. No.: WO2008/063675
PCT Pub. Date: May 29, 2008

(65) Prior Publication Data
US 2010/0150876 A1 Jun. 17, 2010

Related U.S. Application Data

(60) Provisional application No. 60/867,135, filed on Nov. 24, 2006.

(51) Int. Cl.
*C12N 5/071* (2010.01)
*A61K 35/12* (2006.01)

(52) U.S. Cl.
CPC ....... *C12N 5/0678* (2013.01); *A01K 2267/0325* (2013.01); *A61K 35/12* (2013.01); *C12N 2500/42* (2013.01); *C12N 2500/44* (2013.01); *C12N 2501/11* (2013.01); *C12N 2501/235* (2013.01); *C12N 2533/52* (2013.01)

(58) Field of Classification Search
None
See application file for complete search history.

(56) References Cited

U.S. PATENT DOCUMENTS

| | | | |
|---|---|---|---|
| 4,714,680 A | 12/1987 | Civin | |
| 4,965,204 A | 10/1990 | Civin | |
| 5,035,994 A | 7/1991 | Civin | |
| 5,061,620 A | 10/1991 | Tsukamoto et al. | |
| 5,130,144 A | 7/1992 | Civin | |
| 5,486,359 A | 1/1996 | Caplan et al. | |
| 5,589,376 A | 12/1996 | Anderson et al. | |
| 5,602,301 A | 2/1997 | Field | |
| 5,635,386 A | 6/1997 | Palsson et al. | |
| 5,648,248 A | 7/1997 | Zenke et al. | |
| 5,654,183 A | 8/1997 | Anderson et al. | |
| 5,672,499 A | 9/1997 | Anderson et al. | |
| 5,733,727 A | 3/1998 | Field | |
| 5,827,735 A | 10/1998 | Young et al. | |
| 5,843,425 A | 12/1998 | Sachs et al. | |
| 5,843,780 A | 12/1998 | Thomson | |
| 5,906,934 A | 5/1999 | Grande et al. | |
| 5,928,943 A | 7/1999 | Franz et al. | |
| 6,015,671 A | 1/2000 | Field | |
| 6,030,833 A | 2/2000 | Seebach et al. | |
| 6,090,622 A | 7/2000 | Gearhart et al. | |
| 6,090,625 A | 7/2000 | Abuljadayel | |
| 6,146,888 A | 11/2000 | Smith et al. | |
| 6,200,806 B1 | 3/2001 | Thomson | |
| 6,214,369 B1 | 4/2001 | Grande et al. | |
| 6,271,436 B1 | 8/2001 | Piedrahita et al. | |
| 6,280,718 B1 | 8/2001 | Kaufman et al. | |
| 6,306,575 B1 | 10/2001 | Thomas et al. | |
| 6,361,997 B1 | 3/2002 | Huss | |
| 6,387,369 B1 | 5/2002 | Pittenger et al. | |
| 6,610,535 B1 * | 8/2003 | Lu et al. | 435/325 |
| 2001/0005591 A1 | 6/2001 | Qasba et al. | |
| 2001/0012513 A1 | 8/2001 | Robl et al. | |
| 2001/0024824 A1 | 9/2001 | Moss et al. | |
| 2001/0024825 A1 | 9/2001 | Thomson | |
| 2001/0033834 A1 | 10/2001 | Wilkison et al. | |
| 2001/0046489 A1 | 11/2001 | Habener et al. | |
| 2002/0061587 A1 | 5/2002 | Anversa | |
| 2002/0098167 A1 | 7/2002 | Anversa et al. | |
| 2002/0164794 A1 | 11/2002 | Wernet | |
| 2002/0192816 A1 * | 12/2002 | Roberts et al. | 435/366 |
| 2003/0054973 A1 | 3/2003 | Anversa | |
| 2003/0157078 A1 | 8/2003 | Hall et al. | |
| 2003/0186439 A1 | 10/2003 | Nakauchi et al. | |
| 2004/0033217 A1 | 2/2004 | Vanguri et al. | |
| 2004/0107453 A1 | 6/2004 | Furcht et al. | |
| 2004/0229351 A1 | 11/2004 | Rodriguez et al. | |
| 2005/0283844 A1 | 12/2005 | Furcht et al. | |
| 2006/0008450 A1 | 1/2006 | Verfaillie et al. | |
| 2006/0263337 A1 | 11/2006 | Maziarz et al. | |
| 2007/0009500 A1 | 1/2007 | Blazar et al. | |

FOREIGN PATENT DOCUMENTS

CA 2191655 A1 6/1997
EP 0627487 A2 12/1994

(Continued)

OTHER PUBLICATIONS

Zulewski et al., Multipotential Nestin-Positive Stem Cells Isolated From Adult Pancreatic Islets Differentiate Ex Vivo Into Pancreatic Endocrine, Exocrine, and Hepatic Phenotypes, 2001, Diabetes 50(3): 521-533.*
Suzuki et al., Establishment of Clonal Colony-Forming Assay System for Pancreatic Stem/Progenitor Cells, 2002, Cell Transplantation 11(5): 451-453.*
Kruse et al., Pluripotency of adult stem cells derived from human and rat pancreas, 2004, Applied Physics A 79(7): 1617-1624.*
Skalli et al., Alpha-smooth muscle actin, a differentiation marker of smooth muscle cells, is present in microfilamentous bundles of pericytes, 1989, Journal of Histochemistry & Cytochemistry 37(3): 315-321.*
"Australian Applicaton Serial No. 2007321928, Examiner's Report mailed Jul. 28, 2012", 3 pgs.
"International Application Serial No. PCT/US2007/024415, International Search Report mailed May 23, 2008", P220, 9 pgs.

(Continued)

*Primary Examiner* — Robert Yamasaki
(74) *Attorney, Agent, or Firm* — Schwegman Lundberg & Woessner, P.A.

(57) ABSTRACT

The present invention relates to endodermal progenitor cells and methods of isolation, culture, differentiation and use thereof.

19 Claims, 15 Drawing Sheets

(56) References Cited

FOREIGN PATENT DOCUMENTS

| WO | WO-95/03062 A1 | 2/1995 |
|---|---|---|
| WO | WO-95/10599 A1 | 4/1995 |
| WO | WO-95/14079 A1 | 5/1995 |
| WO | WO 96/16163 A1 | 5/1996 |
| WO | WO-96/23870 A1 | 8/1996 |
| WO | WO-96/28539 A1 | 9/1996 |
| WO | WO-99/11758 A1 | 3/1999 |
| WO | WO-99/11758 A2 | 3/1999 |
| WO | WO-99/15629 A1 | 4/1999 |
| WO | WO-99/16863 A1 | 4/1999 |
| WO | WO-99/23205 A1 | 5/1999 |
| WO | WO-99/27076 A1 | 6/1999 |
| WO | WO-99/35243 A2 | 7/1999 |
| WO | WO-99/53021 A1 | 10/1999 |
| WO | WO-00/12682 A1 | 3/2000 |
| WO | WO-00/32140 A1 | 6/2000 |
| WO | WO-00/57922 A1 | 10/2000 |
| WO | WO-01/04268 A1 | 1/2001 |
| WO | WO-01/05944 A1 | 1/2001 |
| WO | WO-01/08691 A | 2/2001 |
| WO | WO-01/11011 A2 | 2/2001 |
| WO | WO-01/21766 A2 | 3/2001 |
| WO | WO-01/21767 A2 | 3/2001 |
| WO | WO-01/23528 A1 | 4/2001 |
| WO | WO-01/29206 A1 | 4/2001 |
| WO | WO-01/34776 A1 | 5/2001 |
| WO | WO-01/39784 A1 | 6/2001 |
| WO | WO-01/51610 A1 | 7/2001 |
| WO | WO-01/53461 A1 | 7/2001 |
| WO | WO-01/62899 A2 | 8/2001 |
| WO | WO-01/62901 A2 | 8/2001 |
| WO | WO-01/66697 A2 | 9/2001 |
| WO | WO-01/68815 A1 | 9/2001 |
| WO | WO-02/08388 A2 | 1/2002 |
| WO | WO-02/34890 A2 | 5/2002 |
| WO | WO-02/063962 A1 | 8/2002 |
| WO | WO-02/064748 A2 | 8/2002 |
| WO | WO-02/064755 A2 | 8/2002 |
| WO | WO-03/050249 A2 | 6/2003 |
| WO | WO-03/080649 A2 | 10/2003 |
| WO | WO-03/087333 A2 | 10/2003 |
| WO | WO-03/101202 A1 | 12/2003 |
| WO | WO-2004/015077 A2 | 2/2004 |
| WO | WO-2004/015091 A2 | 2/2004 |
| WO | WO-2004/050859 A2 | 6/2004 |
| WO | WO-2005/007073 A2 | 1/2005 |
| WO | WO-2005/016250 A2 | 2/2005 |
| WO | WO-2005/021716 A2 | 3/2005 |
| WO | WO-2005/056026 A1 | 6/2005 |
| WO | WO-2005/113748 A2 | 12/2005 |
| WO | WO-2006/047743 A2 | 5/2006 |
| WO | WO-2006/047743 A3 | 5/2006 |
| WO | WO-2006/086639 A1 | 8/2006 |
| WO | WO-2006/121428 A1 | 11/2006 |
| WO | WO-2006/121454 A2 | 11/2006 |
| WO | WO-2007/047509 A2 | 4/2007 |
| WO | WO-2008/063675 A2 | 5/2008 |
| WO | WO-2008/063675 C2 | 5/2008 |

OTHER PUBLICATIONS

"International Application Serial No. PCT/US2007/024415, Written Opinion mailed May 23, 2008", P237, 9 pgs.
"Israeli Application Serial No. 198892, Office Action Response filed Jul. 24, 2012", 5 pgs.
"Israeli Application Serial No. 198892, Response filed Jul. 25, 2012 to Office Action mailed Sep. 25, 2011".
"Israeli Application Serial No. 198892, Office Action mail date Sep. 25, 2011", 2 pgs.
Abo-Zena, R. A, et al., "Immunomodulation in stem-cell transplantation", Current Opinion in Pharmacology; 2(4), (Aug. 2002), 452-457.
Aldhous, P., et al., "Flawed Stem Cell Data Withdrawn", [on-line]. [retrieved on Feb. 23, 2007]. Retrieved From the Internet: <URL: http:/www.newscientist.com/article.ns?id=mg19325915.200 &print=true>, 2 pgs.
Aldhous, P., et al., "Fresh Questions on Stem Cell Findings", New Scientist, (2007), 12-13.
Alfonso, Z., et al., "Osteoblast Precursor Cells Are Found in the Low-Density Fraction of Umbilical Cord Blood", Blood, 94(10)(Suppl. 1, Part 2), (Abstract #3897), (Nov. 15, 1999), p. 161b.
Ali, N. N, et al., "Derivation of Type II Alveolar Epithelial Cells from Murine Embryonic Stem Cells", Tissue Engineering, Larchmont, vol. 8 (4), (Aug. 2002), 541-550.
Amit, M., et al., "Clonally Derived Human Embryonic Stem Cell Lines Maintain Pluripotency and Proliferative Potential for Prolonged Periods of Culture", Developmental Biology, 227(2), (2000), 271-278.
Application No. 198892, "Office Action Mailed Jul. 20, 2009 Application No. 198892", Notification Prior to Examination, 2.
Aranguren, X. L, et al., "Human Multipotent Adult Progenitor Cells(MAPC) can Differentiate in Vitro and Vivo into Arterial and Venous Endothelium", Circulation, 112(17), (Oct. 2005), U92.
Aranguren, X. L, et al., "The Arterial and Venous Potential of Human MAPC and AC133 Derived Endothelial Cells is Modulated by Activation of Notch and Patched Ligands", Experimental Hematology, 33(7), (Jul. 2005), 76-77.
Asahara, T., et al., "Stem Cell Therapy and Gene Transfer for Regeneration", Gene Therapy, 7(6), (2000), 451-457.
Asahara, Takayuki, "Isolation of Putative Progenitor Endothelial Cells for Angiogenesis", Science, 275(5302), (Feb. 14, 1997), 964-967.
Bayens, L., et al., "In vitro generation of insulin producing beta cells from adult exocrine pancreatic cells", Diabetologia, Clinical and Experimental Diabetes and Metabolism, Springer-Verlag, BE, vol. 48, No. 1, ISSN: 1432-0428, (Jan. 1, 2005), 49-57 pgs.
Behnan, S. M, et al., "Isolation and characterisation of immature hepatic system cells derived from unmanipulated rat liver", Blood, vol. 102, No. 11, & 45th Annual Meeting of the American Society of Hematology; San Diego; CA, USA, ISSN: 0006-4971, (Dec. 6-9, 2003), 336a pg.
Beltrami, A. P., et al., "Evidence That Human Cardiac Myocytes Divide After Myocardial Infarction", The New England Journal of Medicine, 344(23), (Jun. 7, 2001), 1750-1757.
Ben-Shushan, E., et al., "Rex-1, a Gene Encoding a Transcription Factor Expressed in the Early Embryo, is Regulated via Oct-3/4 and Oct-6 Binding to an Octamer Site and a Novel Protein, Rox-1, Binding to an Adjacent Site", Molecular & Cellular Biology, 18(4), (Apr. 1998), 1866-1878.
Bianco, P., et al., "Stem Cells in Tissue Engineering", Nature, 414, (Nov. 1, 2001), 118-121.
Bix, M., et al., "Rejection of Class I MHC-Deficient haemopoietic cells by irradiated MHC-matched mice", Nature; 349(6307), (Jan. 24, 1991), 329-331.
Bjornson, C. R., et al., "Turning Brain Into Blood: A Hematopoietic Fate Adopted by Adult Neural Stem Cells in vivo", Science, 283(5401), (Jan. 22, 1999), 534-537.
Blume, K. G., et al., "A Review of Autologous Hematopoietic Cell Transplantation .", Biology of Blood and Marrow Transplantation, 6, (2000), 1-12.
Bongso, A., et al., "The Growth of Inner Cell Mass Cells From Human Blastocysts", Theriogenology, 41, (1994), p. 167.
Bonner-Weir, S., "New sources of pancreatic beta-cells", Nat Biotechnol., 23(7), (Jul. 2005), 857-61.
Brustle, O., et al., "Embryonic Stem Cell-Derived Glial Precursors: A Source of Myelinating Transplants", Science, 285(5428), (Jul. 30, 1999), 754-756.
Campion, D. R., "The Muscle Satellite Cell: A Review", International Review of Cytology, 87, (1984), 225-251.
Cargill, M., et al., "Characterization of Single-Nucleotide Polymorphisms in Coding Regions of Genes", Nature Genetics, 22, (Jul. 1999), 231-238.

(56) References Cited

OTHER PUBLICATIONS

Cassiede, P., et al., "Osteochondrogenic Potential of Marrow Mesenchymal Progenitor Cells Exposed to TGF-beta1 or PDGF-BB as Assay invivo and in vitro", Journal of Bone and Mineral Research., 11 (9), (1996), 1264-1273.
Chalmers-Redman, R. M., et al., "In Vitro Propagation and Inducible Differentiation of Multipotential Progenitor Cells From Human Fetal Brain", Neuroscience, 76(4), (1997), 1121-1128.
Check, E, "Stem-Cell Paper Corrected", Nature Publishing Group, (2007), p. 763.
Chen, J., et al., "Therapeutic Benefit of Intravenous Administration of Bone Marrow Stromal Cells After Cerebral Ischemia in Rats", Stroke, 32(4), (2001), 1005-1011.
Chi, K. R., "Adult Stem Cell Figure Retracted", [on-line]. 2007(c), TheScientist. [retrieved on Jun. 13, 2007]. Retrieved from the Internet: <URL: http://www.the-scientist.com/news/home/53279/>, 5 pgs.
Coultas, L., et al., "Endothelial Cells and VEGF in Vascular Development", Nature, 438(7070), (Dec. 2005), 937-945.
Cutler, C., et al., "Peripheral Blood Stem Cells for Allogeneic Transplantation: A Review", Stem Cells, 19, (2001), 108-117.
Deutsch, G., et al., "A bipotential precursor population for pancreas and liver within the embryonicendoderm", Development, 128(6), (2001), 871-881.
D'Ippolito, G., "Marrow-isolated adult multilineage inducible (MIAMI) cells, a unique population of postnatal young and old human cells with extensive expansion and differentiation potential", J Cell Sci., 117(Pt 14), (Jun. 15, 2004), 2971-81.
D'Lppolito, G., et al., "Marrow-isolated adult multilineage inducible(MIAMI) cells, a unique populationof postnatal expansion and differentiation potential", Journal of Cell Science, Cambridge, University Press, London, GB, vol. 117, No. part 14, ISSN: 0021-9533, (Jun. 15, 2004), 2971-2981 pgs.
Doetschman, T., et al., "Establishment of Hamster Blastocyst-Derived Embryonic Stem (ES) Cells", Developmental Biology, 127(1), (1998), 224-227.
Donovan, P. J., et al., "The End of the Beginning for Pluripotent Stem Cells", Nature, 414, (Nov. 1, 2001), 92-97.
Erices, A., et al., "Mesenchymal Progenitor Cells in Human Umbilical Cord Blood", British Journal of Haematology, 109, (2000), 235-242.
Etzion, S., et al., "Influence of Embryonic Cardiomyocyte Transplantation on the Progression of Heart Failure in a Rat Model of Extensive Myocardial Infarction", J. Mol. Cell. Cardiol., 33(7), (2001), 1321-1330.
Evans, M. J., et al., "Establishment in Culture of Pluripotential Cells From Mouse Embryos", Nature, 292(5819), (Jul. 9, 1981), 154-156.
First, N. L., et al., "Systems for Production of Calves From Cultured Bovine Embryonic Cells", Reproduction, Fertility and Development, 6(5), (1994), 553-562.
Fujio, K., "Coexpression of stem cell factor and c-kit in embryonic and adult liver", Exp Cell Res., 224(2), (May 1, 1996), 243-50.
Gail, D., et al., "A biopotential precursor population for pancreas and liver within the embryonic endoderm", Develpoment, Company of Biologists, Cambridge, GB, vol. 128, No. 6, ISSN: 0950-1991, (Mar. 15, 2001), 871-881 pgs.
Game, D. S., et al., "Rejection Mechanisms in Transplantation", Wien Klin Wochenschr, vol. 113/20-21, (2001), 832-838.
Geiger, H., et al., "Globin Gene Expression is Reprogrammed in Chimeras Generated by Injecting Adult Hematopoietic Stem Cells Into Mouse Blastocysts", Cell, 93(6), (Jun. 12, 1998), 1055-1065.
Geissler, E. K., et al., "Effective Use of Donor MHC Class I Gene Therapy in Organ Transplantation: Prevention of Antibody-Mediated Hyperacute Heart Allograft Rejection in Highly Sensitized Rat Receipients", Human Gene Therapy, 11(3), (2000), 459-469.
Gershengorn, M. C., "Epithelial-to-mesenchymal transition generates proliferative human islet precursor cells", Science, 306(5705), (Dec. 24, 2004), 2261-4.
Gmyr, V., et al., "Adult Human Cytokeratin 19-Positive Cells Reexpress Insulin Promoter Factor 1 In Vitro—Further Evidence for Pluripotent Pancreatic Stem Cells in Humans", Diabetes, 49(10), (2000), 1671-1680.
Goodwin, H. S., et al., "Multilineage Differentiation Activity by Cells Isolated From Umbilical Cord Blood: Expression of Bone, Fat, and Neural Markers", Biology of Blood and Marrow Transplantation, 7, (2001), 581-588.
Goolsby, et al., "Hematopoietic Progenitors express neural genes", PNAS, 100(25), 14926-14931.
Gotoh, M., et al., "Crucial role of pancreatic ductal collagenase injection for isolation of pancreatic islets", Horm Metab Res Suppl., 25, (1990), 10-6.
Grigoriadou, K., et al., "MHC Class Ia Molecules Alone Control NK-Mediated Bone Marrow Graft Rejection", European Journal of Immunology, 29(11), (Nov. 1999), 3683-3690.
Gulcher, J., et al., "Population Genetics: Laying the Groundwork for Genetic Disease Modeling and Targeting", Clinical Chemical Laboratory Medicine, 36(8), (1998), 523-727.
Gunsilius, E., et al., "Hematopoietic Stem Cells", Biomedicine & Pharmacotherapy, 55(4), (2001), 186-194.
Gussoni, E., et al., "Dystrophin expression in the mdx mouse restored by stem cell transplantation", Nature, 401, (Sep. 23, 1999), 390-394.
Gussoni, E., et al., "Long-Term Persistence of Donor Nuclei in Duchenne Muscular Dystrophy Patient Receiving Bone Marrow Transplantation", The Journal of Clinical Investigation, 110(6), (Sep. 2002), 807-814.
Hamilton, D. P., "The Tissue Bank's Shaky Underpinnings", Science, 257(5072), (Aug. 14, 1992), p. 869.
Handyside, A., et al., "Towards the Isolation of Embryonal Stem Cell Lines From the Sheep", Development Genes and Evolution, 196(3), (1987), 185-190.
Handyside, A. H., et al., "Use of BRL-Conditioned Medium in Combination With Feeder Layers to Isolate a Diploid Embryonal Stem Cell Line", Roux's Archives of Developmental Biology, 198(1), (1989), 48-56.
Heremans, Y., "Recapitulation of embryonic neuroendocrine differentiation in adult human pancreatic duct cells expressing neurogenin 3.", J Cell Biol., 159(2), (Oct. 28, 2002), 303-12.
Hilton, D. J., et al., "Distribution and Comparison of Receptors for Leukemia Inhibitory Factor on Murine Hemopoietic and Hepatic Cells", Journal of Cellular Physiology, 146(2), (1991), 207-215.
Holden, C., et al., "Stem Cells: Controversial Marrow Cells Coming", Science, 315(760), (2007), 760-761.
Hughes, S., "Cardiac Stem Cells", Journal of Pathology, 197(4), (2002), 468-478.
Iannaccone, P. M., et al., "Pluripotent Embryonic Stem Cells From the Rat are Capable of Producing Chimeras", Developmental Biology, 163(1), (1994), 288-292.
Ide, H., "Formation of ductular structures in vitro by rat pancreatic epithelial oval cells", Exp Cell Res., 209(1), (Nov. 1993), 38-44.
Iso, T., et al., "Notch Signaling in Vascular Development", Arteriosclerosis Thrombosis and Vascular Biology, 23(4), (Apr. 2003), 543-553.
Jeffers, M., "Hepatocyte growth factor/scatter factor-Met signaling induces proliferation, migration, and morphogenesis of pancreatic oval cells", Cell Growth Differ., 7(12), (Dec. 1996), 1805-13.
Jessy, L., et al., "Metaplasia in the pancreas", Differentiation, vol. 73, No. 6, ISSN: 0301-4681, (Jul. 2005), 278-286 pgs.
Jiang, Y., et al., "Corrigendum—Pluripotency of Mesenchymal Stem Cells Derived From Adult Marrow", Nature, 447, (Jun. 2007), 879-880.
Jiang, Y., et al., "Multipotent Progenitor Cells can be Isolated From Postnatal Murine Bone Marrow, Muscle, and Brain", Experimental Hematology, 30(8), (2002), 896-904.
Jiang, Y., et al., "Multipotent Progenitor Cells can be Isolated From Postnatal Murine Bone Marrow, Muscle, and Brain", Experimental Hematology, 30(8), (Aug. 2002), 896-904.
Jiang, Y., "Pluripotency of mesenchymal stem cells derived from adult marrow", Nature, 418(6893), (Jul. 4, 2002), 41-9.
Jiang, Y., et al., "Pluripotency of Mesenchymal Stem Cells Derived From Adult Marrow", Nature, 418(6893), (Jul. 4, 2002), 41-49.

(56) References Cited

OTHER PUBLICATIONS

Jiang, Y., et al., "Pluripotency of mesenchymal stem cells derived from adult marrow", Nature, Nature Publishing Group; 418 (6893), (Jul. 4, 2002), 41-49.
Jiang, Y., et al., "Pluripotency of Mesenchymal Stem Cells Derived From Adult Marrow", Nature, 418(6893), (2002), 41-49.
Jiao, S., et al., "Long-Term Correction of Rat Model of Parkinson's Disease by Gene Therapy", Nature, 362, (Apr. 1, 1993), 450-453.
Keene, C. D., et al., "Phenotypic Expression of Transplanted Human Bone Marrow-Derived Multipotent Adult Stem Cells Into the Rat CNS", Experimental Neurology, 164(2), (Abstract Only), Seventh Annual Conference of the American Society for Neural Transplantation and Repair (Clearwater, FL, Apr. 27-30, 2000), (Aug. 2000), p. 465.
Kehat, I., et al., "Human Embryonic Stem Cells Can Differentiate Into Myocytes With Structural and Functional Properties of Cardiomyocytes", The Journal of Clinical Investigation, 108(3), (Aug. 2001), 407-414.
Kessler, P. D., et al., "Myoblast Cell Grafting Into Heart Muscle: Cellular Biology and Potential Applications", Annual Review of Physiology, 61, (1999), 219-242.
Klug, M. G., et al., "Genetically Selected Cardiomyocytes From Differentiating Embryonic Stem Cells Form Stable Intracardiac Grafts", The Journal of Clinical Investigation, 98(1), (1996), 216-224.
Knight, B., "Jekyll and Hyde: evolving perspectives on the function and potential of the adult liver progenitor (oval) cell", Bioessays, 27(11), (Nov. 2005), 1192-202.
Kocher, A. A., et al., "Neovascularization of Ischemic Myocardium by Human Bone-Marrow-Derived Angioblasts Prevents Cardiomyocyte Apoptosis, Reduces Remodeling and Improves Cardiac Function", Nature Medicine, 7(4), (Apr. 2001), 430-436.
Koh, G. Y., et al., "Differentiation and Long-Term Survival of C2C12 Myoblast Grafts in Heart", The Journal of Clinical Investigation, 92(3), (Sep. 1993), 1548-1554.
Kovacevic, M., et al., "Erythroid Progenitor Cells from Pig Bone Marrow and Peripheral Blood", The Veterinary Journal, 158, www.idealibrary.com, (1999), 196-203.
Krause, D. S, et al., "Multi-Organ, Multi-Lineage Engraftment by a Single Bone Marrow-Derived Stem Cell", Cell, 105, (May 2001), 369-377.
Kuznetsov, S. A., et al., "Factors Required for Bone Marrow Stromal Fibroblast Colony Formation in Vitro", British Journal of Haematology, 97(3), (Jun. 1997), 561-570.
Lacy, P. E, et al., "Method for the isolation of intact islets of Langerhans from the rat pancreas", Diabetes, 16(1), (Jan. 1967), 35-9.
Lagasse, et al., "Purified hematopoietic stem cells can differentiate into hepatocytes in vivo", nature Medicine,6(11), 1229-1234.
Lamming, C. E. D., et al., "Spontaneous Circulation of Myeloid-Lymphoid-Initiating Cells and SCID-Repopulating Cells in Sickle Cell Crisis", Journal of Clinical Investigation, 111(6), (Mar. 2003), 811-819.
Lansdorp, "Role of telomerase in Hematopoietic stem cells", Ann. N.Y. Acad. Sci 1044, 220-227.
Lennon, Donald P., et al., "A Chemically Defined Medium Supports in vitro Proliferation and Maintains the Osteochondral Potential of Rat Marrow-Derived Mesenchymal Stem Cells", Experimental Cell Research, 219 (1), (1995), 211-222.
Lerner, M., et al., "Stem Cell Study Was Flawed, U Panel Finds", [on-line]. StarTribune.com. [retrieved on Feb. 23, 2007]. Retrieved from the Internet: <URL: http://www.startribune.com/1244/story/1020101.html>, 4 pgs.
Lodie, T. A, et al., "Systematic Analysis of Reportedly Distinct Populations of Multipotent Bone Marrow-Derived Stem Cells Reveals a Lack of Distinction", Tissue Engineering, 8(5), (2002), 739-751.
Lovell-Badge, R., "The Future for Stem Cell Research", Nature, 414, (Nov. 1, 2001), 88-91.
Malancha, T., et al., "The defined combination of growth factor controls generation of long-term-replicating islet progenitor-like cells from cultures of adult mouse pancreas", System Cells(Miamisburg), vol. 24, No. 7, ISSN: 1066-5099, (Jul. 2006), 1738-1749 pgs.
Marmur, R., et al., "Isolation and Developmental Characterization of Cerebral Cortical Multipotent Progenitors", Developmental Biology, 204(2), (1998), 577-591.
McLaren, A., "Ethical and Social Considerations of Stem Cell Research", Nature, 414, (Nov. 2001), 129-131.
Menasche, P., et al., "Myoblast Transplantation for Heart Failure", The Lancet, 357(9252), (2001), 279-280.
Menasche, P., "Skeletal Muscle Satellite Cell Transplantation", Cardiovascular Research, 58, (2003), 351-357.
Miller, J. S., et al., "Ex Vivo Culture of CD34+/Lin-/DR-Cells in Stroma-Derived Soluble Factors, Interleukin-3, and Macrophage Inflammatory Protein-1 alpha Maintains Not Only Myeloid But Also Lymphoid Progenitors in a Novel Switch Culture Assay", Blood, 91(12), (1998), 4516-4522.
Noonan, K. E., "Limitations on the Usefulness of Adult Stem Cells", [on-line]. [retrieved on Mar. 1, 2007]. Retrieved from the Internet: <URL: http://patentdocs.typepad.com/patent_docs/2007/02/limitations_on_html, 3 pgs.
Oh, S. H., "Hepatic oval 'stem' cell in liver regeneration", Semin Cell Dev Biol., 13(6), (Dec. 2002), 405-9.
Orlic, D., "Bone Marrow Cells Regenerate Infarcted Myocardium", Nature, 410(6829), (Apr. 5, 2001), 701-705.
Orlic, D., et al., "Transplanted Adult Bone Marrow Cells Repair Myocardial Infarcts in Mice", Ann. N.Y. Acad. Sci., 938, (2001), 221-230.
Ott, H. C., et al., "Cell-Based Cardiovascular Repair", Basic Res Cardiol, 100, (2005), 504-517.
Ouziel-Yahalom, L., "Expansion and redifferentiation of adult human pancreatic islet cells", Biochem Biophys Res Commun., 341(2), (Mar. 10, 2006), 291-8.
Pera, M. F., et al., "Human Embryonic Stem Cells", Journal of Cell Science, 113(1), (2000), 5-10.
Petersen, B. E., "Hepatic oval cells express the hematopoietic stem cell marker Thy-1 in the rat", Hepatology, 27(2), (Feb. 1998), 433-45.
Petersen, B. E., "Mouse A6-positive hepatic oval cells also express several hematopoietic stem cell markers", Hepatology, 37(3), (Mar. 2003), 632-40.
Peterson, B. E, et al., "Mouse A6-positive hepatic oval cells also express several hematopoietic stem cell markers", Hepatology, vol. 37, No. 3, ISSN: 0270-9139, (Mar. 2003), 632-640 pgs.
Pincock, S., "Adult Stem Cell Report Questioned", [online]. (c) 2007, TheScientist.com. [retrieved on Feb. 27, 2007]. Retrieved from the Internet: <URL: http://www.the-scientist.com/news/display/52892/>, 4 pgs.
Pittenger, M. F., et al., "Multilineage Potential of Adult Human Mesenchymal Stem Cells", Science, 284 (5411), (Apr. 2, 1999), 143-147.
Prosper, F., et al., "Phenotypic and Functional Characterization of Long-Term Culture-Initiating Cells Present in Peripheral Blood Progenitor Collections of Normal Donors Treated With Granulocyte Colony-Stimulating Factor", Blood, 88(6), (1996), 2033-2042.
Punzel, M., et al., "The Myeloid-Lymphoid Initiating Cell (ML-IC) Assay Assesses the Fate of Multipotent Human Progenitors In Vitro", Blood, 93(11), (Jun. 1, 1999), 3750-3756.
Qi, H., et al., "Identification of Genes Responsible for Bone Differentiation From Human Bone Marrow Derived Multipotent Adult Stem Cells (MASC)", Blood, 96(11)(Part 1), (Nov. 16, 2000), 70a-71a.
Quirici, N., et al., "Differentiation and Expansion of Endothelial Cells from Human Bone Marrow CD133+ Cells", British Journal of Haematology, 115(1), (Oct. 2001), 186-194.
Raptis, A., et al., "Polymorphoism in CD33 and CD34 Genes: a Source of Minor Histocompatibility Antigens on Haemopoietic Progenitor Cells?", British Journal of Haematology, 102 (5), (1998), 1354-1358.
Reffelmann, T., et al., "Cellular Cardiomyoplasty—Cardiomyocytes, Skeletal Myoblasts, or Stem Cells for Regenerating Myocardium and Treatment of Heart Failure?", Cardiovascular Research, 58(2), (2003), 358-368.

(56) References Cited

OTHER PUBLICATIONS

Reinecke, H., et al., "Skeletal Muscle Stem Cells Do Not Transdifferentiate Into Cardiomyocytes After Cardiac Grafting", J. Mol. Cell Cardiol., 34(2), (2002), 241-249.
Reya, T., "Stem Cells, Cancer, and Cancer Stem Cells", Nature, 414, (Nov. 1, 2001), 105-111.
Reyes, M., et al., "Characterization of Multipotent Adult Progenitor Cells, A Subpopulation of Mesenchymal Stem Cells", Annals of the New York Academy of Science, 938, (2001), 231-235.
Reyes, M., et al., "Origin of Endothelial Progenitors in Human Post-Natal Bone Marrow.", Blood, 98(11), Part 1., (Dec. 11, 2001), 821A.
Reyes, M., et al., "Origin of Endothelial Progenitors in Human Postnatal Bone Marrow", The Journal of Clinical Investigation, 109(3), (2002), 337-346.
Reyes, M., et al., "Purification and ex vivo Expansion of Postnatal Human Marrow Mesodermal Progenitor Cells", Blood, 98(9), (2001), 2615-2625.
Robinson, C. J, et al., "The Splice Variants of Vascular Endothelial Growth Factor(VEGF) and their Receptors", Journal of Cell Science, 114(5), (Mar. 2001), 853-865.
Rosfjord, Edward, et al., "The octamer motif present in the REX-1 promoter binds OCT-1 and OCT-3 expressed by EC cells and eS cells", Biochem. and Biophysical Res. Comm., 203 (3), , (1994), pp. 1795-1802.
Rosner, M. H., et al., "Oct-3 is a Maternal Factor Required for the First Mouse Embryonic Division", Cell, 64(6), (1991), 1103-1110.
Ruhnke, M., "Differentiation of in vitro-modified human peripheral blood monocytes into hepatocyte-like and pancreatic islet-like cells", Gastroenterology, 128(7), (Jun. 2005), 1774-86.
Sakai, T., et al., "Fetal Cell Transplantation: A Comparision of Three Cell Types", J. Thorac. Cardiovasc. Surg., 118(4), (1999), 715-724.
Schuldiner, M., et al., "Effects of Eight Growth Factors on the Differentiation of Cells Derived From Human Embryonic Stem Cells", Proc. Natl. Acad. Sci. USA, 97(21), (Oct. 10, 2000), 11307-11312.
Schwartz, R. E., "Multipotent Adult Progenitor Cells From Bone Marrow Differentiate Into Functional Hepatocyte-Like Cells", J. Clin. Invest., 109(10), (May 2002), 1291-1302.
Seaberg, R. M., "Clonal identification of multipotent precursors from adult mouse pancreas that generate neural and pancreatic lineages", Nat Biotechnol, 22(9), (2004), 1115-24.
Serafini, M., et al., "Hematopoietic Reconstitution by Multipotent Adult Progenitor Cells: Precursors to Long-Term Hematopoietic Stem Cells", The Journal of Experimental Medicine, 204(1), (and correction, J. Exp. Med., 204(7) (2007), 2 pgs.), (2007), 129-139.
Shmelkov, S. V, et al., "Cytokine Preconditioning Promotes Codifferentiation of Human Fetal Liver CD133+ STem Cells into Angiomyogenic Tissue", Circulation, 111(9), (Mar. 8, 2005), 1175-1183.
Sigurjonsson, et al., "Adult human hematopoietic stem cells produce neurons efficiently in the regerenating chicken embryo spinal cord.", PNAS 102(14), 5227-5232.
Sohn, R. L., et al., "Stem Cell Therapy for Muscular Dystrophy", Expert Opinion Biol Ther, vol. 4(1), (2004), 1-9.
Stalmans, I., et al., "Arteriolar and Venular Patterning in Retinas of Mice Selectively Expressing VEGF Isoforms", Journal of Clinical Investigation, 109(3), (Feb. 2002), 327-336.
Suzuki, A,, "Prospective isolation of multipotent pancreatic progenitors using flow-cytometric cell sorting", Diabetes, 53(8), (Aug. 2004), 2143-52.
Suzuki, A., et al., "Clonal identification and characterization of self-renewing pluripotent system cells in the developing liver", The Journal of Cell Biology, Rockefeller, University Press, US, vol. 156, No. 1, ISSN: 0021-9525, (Jan. 7, 2002), 173-184 ogs.
Ta, M., et al., "The defined combination of growth factors controls generation of long-term-replicating islet progenitor-like cells from cultures of adult mouse pancreas", Stem Cells, 24(7), (Jul. 2006), 1738-49.
Takahashi, T., et al., "Ischemia- and Cytokine-Induced Mobilization of Bone Marrow-Derived Endothelial Progenitor Cells for Neovascularization", Nature Medicine, 5(4), (1999), 434-438.

Talbot, N. C., et al., "Alkaline Phosphatase Staining of Pig and Sheep Epiblast Cells in Culture", Molecular Reproduction and Development, 36(2), (1993), 139-147.
Taylor, D. A., "Cell-Based Myocardial Repair: How Should We Proceed?", Int. J. Cardiol., 95(Suppl. 1):, (2004), S8-S12.
Temple, S., "The Development of Neural Stem Cells", Nature, 414, (Nov. 1, 2001), 112-117.
Terstappen, L. W., et al., "Sequential Generations of Hematopoietic Colonies Derived From Single Nonlineage-Committed CD34+CD38− Progenitor Cells", Blood, 77(6), (1991), 1218-1227.
Thompson, L., "Fetal Transplants Show Promise", Science, 257(5072), (Aug. 14, 1992), 868, 870.
Thomson, J. A., et al., "Embryonic Stem Cell Lines Derived From Human Blastocysts", Science, 282(5391), (Nov. 6, 1998), 1145-1147.
Thomson, J. A., et al., "Pluripotent Cell Lines Derived From Common Marmoset (*Callithrix jacchus*) Blastocysts", Biology of Reproduction, 55, (1996), 254-259.
Tolar, J., et al., "Host factors that impact the biodistribution and persistence of multipotent adult progenitor cells", Blood; 107(10), (May 15, 2006), 4182-4188.
Tolar, J., et al., "Multipotent Adult Progenitor Cells (MAPCs) Reduce Glycosaminoglycan (GAG) Accumulation in a Murine Model of Hurler Syndrome (MPS 1H)", 45th Annual Meeting of the American Society of Hematology, Blood 102 (11), ISSN: 0006-4971, (Nov. 16, 2003), 839a.
Tolar, J., et al., "Real-Time In Vivo Biodistribution of Multipotent Adult Progenitor Cells (MAPC): Role of the Immune System in MAPC Resistance in Non-Transplanted and Bone Marrow Transplanted Mice", Blood; 104(11), (Nov. 2004), 147A-148A.
Tolar, J., et al., "Real-Time in Vivo Imaging of Stem Cells Following Transgenesis by Transposition", Molecular Therapy, Academic Press; 12 (1), (Apr. 12, 2005), 42-48.
Tolar, J., et al., "The in Utero Transfer of Murine Multipotent Adult Progenitor Cells (MAPCs) Result in Brain and Liver Differentiation", 43rd Annual Meeting of the American Society of Hematology,Blood 98 (11), ISSN: 0006-4971, (Nov. 16, 2001), 475a.
Toma, J. G., et al., "Isolation of Multipotent Adult Stem Cells From the Dermis of Mammalin Skin", Nature Cell Biology, 3(9), (2001), 778-784.
Tomita, S., et al., "Autologous Transplantation of Bone Marrow Cells Improves Damaged Heart Function", Circulation, 100(19)(Suppl.), (1999), II-247-II-256.
Utrizberea, J. A., et al., "Therapies in Muscluar Dystrophy: Current Concepts and Future Prospects", European Neurology, 43, (2000), 127-32.
Verfaillie, C. M., "Adult Stem Cells: Assessing the Case for Pluripotency", TRENDS in Cell Biology, 12(11), (2002), 502-508.
Verfaillie, C., "Letter to the Editor", Experimental Hematolog, (attaching Supplemental Information for Verfaillie Corrigendum—Pluripotency of Mesenchymal Stem Cells Derived from Adult Marrow, (2007), 2 pgs.
Verfaillie, C. M., "Meeting Report on an NHLBI Workshop on Ex Vivo Expansion of Stem Cells, Jul. 29, 1999, Washington, D. C. National Heart Lung and Blood Institute", Experimental Hematology, 28(4), (Apr. 2000), 361-364.
Verfaillie, C. M., "Optimizing Hematopoietic Stem Cell Engraftment: A Novel Role for Thrombopietin", Journal of Clinical Investigation, 110, (2002), 303-304.
Wade, N., et al., "Scientists Herald a Versatile Adult Cell", [online]. The New York Times, Jan. 25, 2002. Retrieved from the Internet: <URL: http://query.nytimes.com/gst/fullpage.html?sec=health &res=940DEEDD163AF936A15752C0A9649C8B63>, 2 pgs.
Wang, J. S., et al., "The Coronary Delivery of Marrow Stromal Cells for Myocardial Regeneration: Pathophysiologic and Therapeutic Implications", J. Thorac. Cardiovasc. Surg., 122(4), (2001), 699-705.
Wang, X., "The origin and liver repopulating capacity of murine oval cells", Proc Natl Acad Sci U S A., 100 Suppl 1, (Sep. 30, 2003), 11881-8.
Wang, Y., et al., "Enhanced Recovery of Hematopoietic Progenitor and Stem Cells From Cultivated, Postpartum Human Placenta", Blood, 11(98)(Part 1), (Nov. 16, 2001), p. 183a.

(56) References Cited

OTHER PUBLICATIONS

Wernet, P., et al., "Detection of Unrestricted Multipotential Stem Cells in Human Cord Blood", Blood, 98(11)(Part 1), (Abstract #2300), (Nov. 16, 2001), p. 550a.

Westphal, S. P. N., "Adult Bone Marrow Eyed as Source of Stem Cells", [online]. Boston Globe, Jan. 24, 2002. [archived Feb. 6, 2002]. Retrieved from the Internet: <URL: http://www.boston.com/dailyglobe2/024/nation/Adult_bone_marrow_eyed_as_source_of_stem_cells+.shtml>, 1 pg.

Wobus, A. M., et al., "Retinoic Acid Accelerates Embryonic Stem Cell-Derived Cardiac Differentiation and Enhances Development of Ventricular Cardiomyocytes", J. Mol. Cell. Cardiol., 29(6), (1997), 1525-1539.

Xu, C., et al., "Feeder-Free Growth of Undifferentiated Human Embryonic Stem Cells", Nature Biotechnology, 19(10), (2001), 971-974.

Yaffe, D., et al., "Serial Passaging and Differentiation of Myogenic Cells Isolated From Dystrophic Mouse Muscle", Nature, 270, (1977), 725-727.

Yamamoto, K., "Recombinant human betacellulin promotes the neogenesis of beta-cells and ameliorates glucose intolerance in mice with diabetes induced by selective alloxan perfusion", Diabetes, 49(12), (Dec. 2000), 2021-7.

Yang, Y., et al., "Enhanced Recovery of Hematopoietic Progenitor and Stem Cells From Cultivated, Postpartum Human Placenta", Blood, 98(11)(Part 1), (Abstract #769), (Nov. 16, 2001), p. 183a.

Yin, A. H., et al., "AC133, a Novel Marker for Human Hematopoietic Stem and Progenitor Cells", Blood, 90(12), (1997), 5002-5012.

Zalzman, M., "Differentiation of human liver-derived, insulin-producing cells toward the beta-cell phenotype", Diabetes, 54(9), (Sep. 2005), 2568-75.

Zhao, L. R., et al., "Human Bone Marrow Stem Cells Exhibit Neural Phenotypes and Ameliorate Neurological Deficits After Grafting Into the Ischemic Brain of Rats", Experimental Neurology, 174(1), (Mar. 2002), 11-20.

Zhao, L. R., et al., "Immunohistochemical Identification of Multipotent Adult Progenitor Cells From Human Bone Marrow After Transplantation Into the Rat Brain", Brain Research Protocols, 11(1), (2003), 38-45.

Zulewski, H., et al., "Multipotential nestin-positive system cells isolated from adult pancreatic islets differentiate ex vino into pancreatic endocrine, exocrine and hepatic phenotypes", Diabetes, New York, NY, US, vol. 50, No. 3, ISSN: 0012-1797, (Mar. 1, 2001), 521-533 pgs.

Kanj, et al., "Myocardial Ischenia Associated With High-dose Carmustine Infusion.", Cancer, 68 (9), (1991), 1910-1912.

Kelly, L. D., et al., "DNA Microarray Analysis of Genes Regulated During the Differentiation of Embryonic Stem Cells", Molecular Reproduction and Development, 56(2), (2000), 113-123.

Koh, G. Y., et al., "Long-Term Survival of AT-1 Cardiomyocyte Grafts in Syngeneic Myocardium", American Journal of Physiology—Heart and Circulatory Physiology, 264, (1993), H1727-H1733.

Lardon, J., et al., "Metaplasia in the pancreas", Differentiation, vol. 73, No. 6, (Jul. 2005), 278-286.

Lewis, I. D., et al., "Multi-Lineage Expansion Potential of Primative Hematopoietic Progenitors: Superiority of Umbilical Cord Blood Compared to Mobilized Peripheral Blood", Experimental Hematology, 28(9), (2000), 1087-1095.

Liu, H., et al., "Myeloid-Lymphoid Initiating Cells (ML-IC) are Highly Enriched in the Rhodamine-c-kit(+)CD33(−)CD38(−) Fracture of Umbilical Cord CD34(+) Cells", Experimental Hematology, 30(6), (2002), 582-589.

Loweel, S., "Stem Cells Show Their Potential", Trends in Cell Biology, 10, (May 2000), 210-211.

Piedrahita, J. A., et al., "Influence of Feeder Layer Typo on the Efficiency of Isolation of Porcine Embryo-Derived Cell Lines", Theriogenology, 34(5), (Nov. 1990), 865-877.

Prockop, D. J., "Marrow Stromal Cells as Stem Cells for Nonhematopoietic Tissues", Science, 276(5309), (Apr. 4, 1997), 71-74.

Qi, H., et al., "Identification of Genes Responsible for Osteoblast Differentiation From Human Mesodermal Progenitor Cells", Proc. Natl. Acad. Sci. USA, 100(6), (Mar. 18, 2003), 3305-3310.

Reddy, S., et al., "Fluorescence-Activated Sorting of Totipotent Embryonic Stem Cells Expressing Developmentally Regulated lacZ Fusion Genes", Proc. Natl. Acad. Sci. USA, 89(15), (1992), 6721-6725.

Richards, M., et al., "Human Feeders Support Prolonged Undifferentiated Growth of Human Inner Cell Masses and Embryonic Stem Cells", Nature Biotechnology, 20, (2002), 933-936.

Roy, V., et al., "Expression and Function of Cell Adhesion Molecules on Fetal Liver, Cord Blood and Bone Marrow Hematopoietic Progenitors: Implications for Anatomical Localization and Developmental Stage Specific Regulation of Hematopoiesis", Experimental Hematology, 27(2), (1999), 302-312.

Simnett, S. J., et al., "Autologous Stem Cell Transplantation for Malignancy: A Systematic Review of the Literature.", Clin Lab Haem, 22, (2000), 61-72.

Sims, M. M., et al., "Production of Fetuses From Totipotent Cultured Bovine Inner Cell Mass Cells", Theriogenology, 39, (1993), p. 313.

Smith, A., "Cell Therapy: In Search of Pluripotency", Current Biology, 8(22), (1998), R802-R804.

Soonpaa, M. H., et al., "Formation of Nascent Intercalated Disks Between Grafted Fetal Cardiomyocytes and Host Myocardium", Science, 264(5155), (Apr. 1, 1994), 98-101.

Spradling, A., et al., "Stem Cells Find Their Niche", Nature, 414, (Nov. 1, 2001), 98-104.

Steinhelper, M. E., et al., "Proliferation in vivo and in Culture of Differentiated Adult Atrial Cardiomycytes From Transgenic Mice", American Journal of Physiology—Heart and Circulatory Physiology, 259, (1990), H1826-H1834.

Thomson, J. A., et al., "Isolation of a Primate Embryonic Stem Cell Line", Proc. Natl. Acad. Sci. USA, 92(17), (Aug. 15, 1995), 7844-7848.

Van Stekelenburg-Hamers, A. E. P., et al., "Isolation and Characterization of Permanent Cell Lines From Inner Cell Mass Cells of Bovine Blastocysts", Molecular Reproduction and Development, 40(4), (1995), 444-454.

Verfaillie, C. M., et al., "Stem Cells: Hype and Reality", Hematology—American Society of Hematology Education Program, (2002), 369-391.

Westphal, S. P., et al., "Ultimate Stem Cell Discovered", New Scientist, (Jan. 23, 2002), 2 pgs.

Xhou, L. J., et al., "CD14+ Blood Monocytes Can Differentiate Into Functionally Mature CD83+ Dendritic Cells", Proc. Natl. Acad. Sci. USA, 93(6), (1996), 2588-2592.

\* cited by examiner

| Target | Sequence | Amplicon Size (bp) | SEQ ID NO: |
|---|---|---|---|
| Actb | F: TGTTACCAACTGGGACGACA | | 19 |
| | R: GGGGTGTTGAAGGTCTCAAA | 165 | 20 |
| Afp | F: GCCCTACAGACCATGAAACAAG | | 21 |
| | R: GTGAAACAGACTTCCTGGTCCT | 149 | 22 |
| CK7 | F: CTCCTGGACTTGGATGGTA | | 23 |
| | R: ACGCTGGTTCTTCAAGGTGT | 229 | 24 |
| CK8 | F: ATCGAGATCACCACCTACCG | | 25 |
| | R: TGAAGCCAGGGCTAGTGAGT | 151 | 26 |
| CK18 | F: CGAGGCACTCAAGGAAGAAC | | 27 |
| | R: GCTGAGGTCCTGAGATTTGG | 130 | 28 |
| CK19 | F: ACCCTCCCGAGATTACAACC | | 29 |
| | R: CAAGGCGTGTTCTGTCTCAA | 160 | 30 |
| Cdh1 | F: ACTGTGAAGGGACGGTCAAC | | 31 |
| | R: GGAGCAGCAGGATCAGAATC | 123 | 32 |
| EpCAM | F: GCTGTCATTGTGGTGGTGTC | | 33 |
| | R: CCCTCCTCAGTTCAGCACTC | 165 | 34 |
| Car2 | F: TCAGGGAGCCCATTACTGTC | | 35 |
| | R: GTTGTCCACCATCGCTTCTT | 98 | 36 |
| Prox1 | F: GAAGGGCTATCACCCAATCA | | 37 |
| | R: TGATGAGCTGCGAGGTAATG | 133 | 38 |
| Gsc | F: GAAGCCCTGGAGAACCTCTT | | 39 |
| | R: ACCAGACCTCCACCTTCTCC | 106 | 40 |
| FoxD3 | F: TACCCAATCCTGGACTCTGC | | 41 |
| | R: GGACGGGTTGAGTTTGCTC | 106 | 42 |
| Sox7 | F: TGTTGACAGATCCCCAAGAA | | 43 |
| | R: CTGGGCACCAGTCAATTACA | 130 | 44 |
| Sox17 | F: CTTTATGGTGTGGGCCAAAG | | 45 |
| | R: CTTCTCTGCCAAGGTCAACG | 121 | 46 |
| Gata4 | F: TCAAACCAGAAAACGGAAGC | | 47 |
| | R: GCATCTCTTCACTGCTGCTG | 146 | 48 |
| Gata6 | F: CAACACAGTCCCCGTTCTTT | | 49 |
| | R: TGGTACAGGCGTCAAGAGTG | 122 | 50 |
| Hnf1β | F: CCGCAATCTCAGAACCTCAT | | 51 |
| | R: AGGCTGCTAGCCACACTGTT | 116 | 52 |
| Hnf3α | F: ACAAGGATGCCTCTCCACAC | | 53 |
| | R: ACCTCAGCATGACATGACCA | 130 | 54 |
| Hnf3β | F: CCCGGGACTTAACTGTAACG | | 55 |
| | R: TCATGTTGCTCACGGAAGAG | 152 | 56 |
| Hnf4 | F: TCTGCGAACTCCTTCTGGAT | | 57 |
| | R: CCGAGGGACGATGTAGTCAT | 137 | 58 |
| Hnf6 | F: CCCTGGAGCAAACTCAAGTC | | 59 |

*FIG. 1A*

| | R:TTGGACGGACGCTTATTTTC | 230 | 60 |
|---|---|---|---|
| Pdx1 | F:AACTTAACCTAGGCGTCGCA | | 61 |
| | R:CATTCGCTTGGCATCAGAAGC | 145 | 62 |
| Nkx6.1 | F:ACTTGGCAGGACCAGAGAGA | | 63 |
| | R:AGAGTTCGGGTCCAGAGGTT | 224 | 64 |
| INS2 | F:GACCCACAAGTGGCACAAC | | 65 |
| | R:TCTACAATGCCACGCTTCTG | 101 | 66 |
| Nestin | F:AGGCTGAGAACTCTCGCTTG | | 67 |
| | R:ATTAGGCAAGGGGGAAGAGA | 167 | 68 |
| Vimentin | F:ATGCTTCTCTGGCACGTCTT | | 69 |
| | R:AGCCACGCTTTCATACTGCT | 206 | 70 |
| Ttr | F:CTTTGCCTCTGGGAAGACC | | 71 |
| | R:CAGAGTCGTTGGCTGTGAAA | 173 | 72 |
| Alb | F:GACAAGGAAAGCTGCCTGAC | | 73 |
| | R:TTCTGCAAAGTCAGCATTGG | 174 | 74 |
| Cyp1a1 | F:ACCTCTTTGGAGCTGGGTTT | | 75 |
| | R:GATAGGGCAGCTGAGGTCTG | 165 | 76 |
| Cyp2b13 | F:CTGGCCACCATGAAAGAGTT | | 77 |
| | R:GGGCTCCCTGGTATTTCTTC | 106 | 78 |
| CD45 | F:TGAAAAGCAGCTGATGGATG | | 79 |
| | R:AATACCCGTGGAATGCTCTG | 123 | 80 |
| PU.1 | F:CGATCACTACTGGGATTTCTCC | | 81 |
| | R:CAAGGTTTGATAAGGGAAGCAC | 235 | 82 |
| Lmo2 | F:TACTACAAGCTGGGACGGAAAT | | 83 |
| | R:ATGTCGGAGTTGATGAGAAGGT | 212 | 84 |
| Scl | F:GGAGATTTCTGATGGTCCTCAC | | 85 |
| | R:AGTAACTTGGCCAGGAAATTGA | 201 | 86 |
| Runx1 | F:TTCAGATGTGCATCGTGTCA | | 87 |
| | R:CCAGCGGTTAGGCTTCATAC | 104 | 88 |
| Gata2 | F:CAGGATGGGTGGAACATACTCT | | 89 |
| | R:CATTTTGCTCTCCAAACAAACA | 216 | 90 |
| Cxcr4 | F:TCCTGCCCACCATCTACTTC | | 91 |
| | R:CCGTCATGCTCCTTAGCTTC | 102 | 92 |
| Ikaros | F:ATATTGTGGCCGGAGCTATAAA | | 93 |
| | R:GCTCCTATCTTGCACAGGTCTT | 159 | 94 |
| Kit | F:TGGGAGTTTCCCAGAAACAG | | 95 |
| | R:AAATGGGCACTTGGTTTGAG | 149 | 96 |
| Blnk | F:AGTCTGCTGAAGAGGCCTTG | | 97 |
| | R:AACGCAACTAGGGTGTACGG | 103 | 98 |
| Flk1 | F:TAAAGGCTCAGGCTGGTGTT | | 99 |
| | R:TGGAGAGCAAACCAACCAAT | 121 | 100 |
| vWF | F:CCACTTGCCACAACAACATC | | 101 |
| | R:TGGACTCACAGGAGCAAGTG | 150 | 102 |
| Cdh5 | F:CTTCAAGCTGCCAGAAAACC | | 103 |
| | R:ATTCGGAAGAATTGGCCTCT | 129 | 104 |

*FIG. 1B*

| CD45+PDPCs ||||
|---|---|---|---|
| TARGET | | ΔCt | EXPRESSION LEVEL | % RELATIVE EXPRESSION (CD45+PDPC VS. F2 OVAL CELL) |
| ENDODERM ||||
| EARLY | Afp | 9.25 | +++ | 2965.08 |
| | Sox7 | 11.95 | +++ | 61.77 |
| | Gata4 | 15.24 | ++ | 0.33 |
| | Gata6 | 9.28 | +++ | 150.52 |
| EPITHELIAL | CK7 | 11.27 | +++ | 6.77 |
| | CK19 | 12.28 | ++ | 1.68 |
| | Cdkl(E) | 10.93 | +++ | 4.59 |
| MESODERM ||||
| | Scl | 12.13 | ++ | 123.54 |
| | Lmo2 | 5.12 | ++++ | 597.94 |
| | HoxB4 | 8.91 | +++ | 145.90 |
| HEMATOPOIETIC | Runx1 | 6.33 | +++ | 561.78 |
| | Gata2 | 14.63 | ++ | 62.85 |
| | Cxcr4 | 3.79 | +++ | 188.56 |
| | Kit | 13.23 | ++ | 5.97 |
| | PU.1 | 4.76 | ++++ | 95.26 |
| | Ikaros | 6.67 | +++ | 179.01 |
| | Blnk | 4.60 | ++++ | 3898.91 |
| ENDOTHELIAL | Flk1 | 9.64 | +++ | 8.69 |
| | Cdh5(VE) | 10.71 | +++ | 1.62 |
| | CD31 | 13.54 | ++ | 3.72 |
| | VWF | 7.35 | +++ | 216.60 |
| OTHER | Nestin | 7.44 | +++ | 332.88 |
| | Vimentin | -0.17 | ++++ | 2200.87 |

*FIG. 3C*

| TARGET | FACS PURIFIED PDPC FRACTIONS | | | | | |
|---|---|---|---|---|---|---|
| | ΔCt | | | | | |
| | CD45+/Sca1 (1) | CD45+/Sca1+ (2) | FOLD CHANGE (2 VS. 1) | % RELATIVE EXPRESSION (2 VS. F2 OVAL CELL) | (1) | (2) |
| Actb | *** | *** | *** | *** | | |
| CK7 | 11.40 | 8.08 | ↑9.99 | 60.71 | | |
| CK19 | 12.34 | 9.04 | ↑9.85 | 12.59 | | |
| Cdh1 | 10.22 | 9.35 | ↑1.83 | 13.82 | | |

|  |  | CD45 + PDPC (d0) | | PDPC DIFFERENTIATION | | | | |
|---|---|---|---|---|---|---|---|---|
|  | TARGET | ΔCt | EXPRESSION LEVEL | AVG ΔCt | St. DEV | EXPRESSION LEVEL | REGULATION (FOLD) | % RELATIVE EXPRESSION (VS. MOUSE TOTAL LIVER) |
| EPITHELIAL MARKERS | CK7 | 11.55 | +++ | 6.22 | *** | +++ | ↑40.22 | 3858.59 |
| | CK8 | 10.78 | +++ | 6.48 | 1.75 | +++ | ↑19.69 | 78.19 |
| | CK18 | 8.94 | +++ | 4.31 | 1.76 | +++ | ↑24.76 | 64.62 |
| | CK19 | 14.37 | ++ | 7.33 | 0.61 | +++ | ↑131.59 | 555.97 |
| | Cdh1 | 13.16 | +− | 8.22 | 1.26 | +++ | ↑30.70 | 55.48 |
| | Car2 | 15.14 | +− | 12.28 | 2.58 | ++ | ↑7.26 | 8.66 |
| ENDODERM TRANSCRIPTION FACTORS | Prox1 | 18.62 | + | 9.56 | 3.35 | +++ | ↑533.74 | 3.54 |
| | Gsc | NOT DETECTED | | 14.72 | 4.16 | ++ | ↑205.07 | 1487.69 |
| | Sox17 | 14.33 | +− | 11.20 | 0.84 | +++ | ↑8.75 | 110.19 |
| | Hnf1β | 17.71 | +− | 8.24 | 2.63 | +++ | ↑709.18 | 152.10 |
| | Hnf3α | NOT DETECTED | | 12.32 | *** | ++ | ↑1082.39 | 7.13 |
| | Hnf3β | NOT DETECTED | | 11.47 | 2.64 | +++ | ↑1951.00 | 15.02 |
| | Hnf4 | 16.60 | ++ | 8.42 | *** | +++ | ↑290.02 | 2.78 |
| | Hnf6 | NOT DETECTED | | 11.68 | 3.81 | +++ | ↑1686.71 | 3.06 |
| PANCREATIC | Pdx1 | 15.10 | ++ | 9.61 | *** | +++ | ↑44.94 | 13.49* |
| | Nkx6.1 | NOT DETECTED | | 9.35 | *** | +++ | ↑8480.89 | 20.67* |
| | INS2 | 14.08 | ++ | 17.06 | *** | ++ | ↓7.89 | 0.00* |
| HEPATIC | Afp | 9.34 | +++ | 14.04 | 0.47 | ++ | ↓26.00 | 1048.31 |
| | Met | 11.06 | +++ | 7.53 | *** | +++ | ↑11.55 | NOT TESTED |
| | Ttr | 12.58 | ++ | 8.17 | 1.39 | +++ | ↑21.26 | 0.20 |
| | Alb | NOT DETECTED | | 13.94 | 0.94 | ++ | ↑352.14 | 0.00 |
| | Cyp1a1 | NOT DETECTED | | 9.57 | *** | +++ | ↑7281.40 | 665.76 |
| | Cyp2b13 | NOT DETECTED | | 9.29 | 2.11 | +++ | ↑8841.04 | 0.78 |
| | CD45 | 7.36 | +++ | 9.87 | *** | +++ | ↓5.70 | 27.36 |

*FIG. 4B*

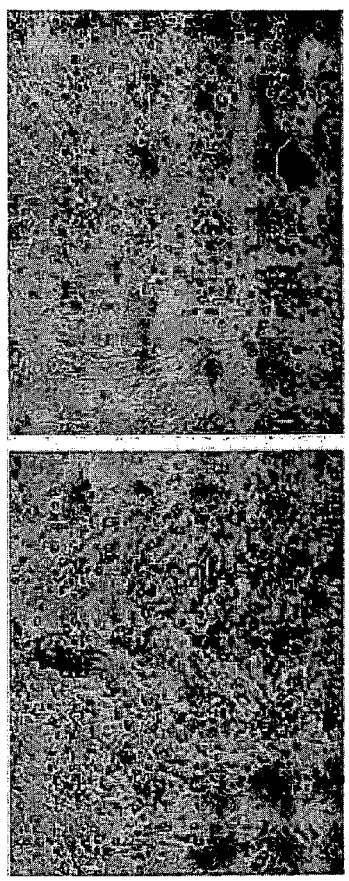
FIG. 8A
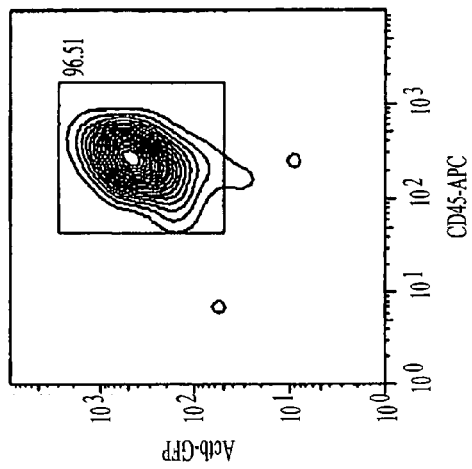
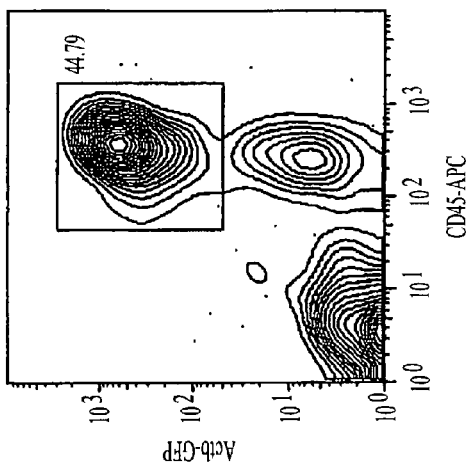
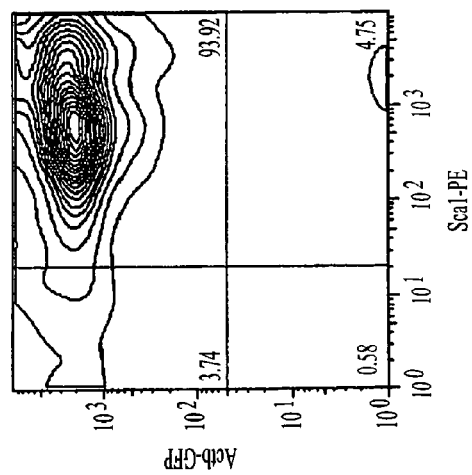
FIG. 8B

| BM Sca1+ (d0) | | BM Sca1+GFP+(d7) PDPC CULTURE | | |
|---|---|---|---|---|
| TARGET | ΔCt | ΔCt | REGULATION (FOLD) | % EXPRESSION (d7 GFP+CD45+ VS. CD45+PDPC) |
| CK7 | 13.58 | 15.25 | ↓3.18 | 7.69 |
| CK8 | 16.67 | 15.74 | ↑1.91 | 3.22 |
| CK18 | 10.09 | 13.78 | ↓12.91 | 3.49 |
| CK19 | 24.84 | 17.09 | ↑215.27 | 15.12 |
| Afp | 11.86 | 11.89 | ↓1.02 | 17.02 |

*FIG. 8C*

```
                              SEQUENCE LISTING

<160> NUMBER OF SEQ ID NOS: 104

<210> SEQ ID NO 1
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 1
catggccttc cgtgttccta                                                     20

<210> SEQ ID NO 2
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 2
ctggtcctca gtgtagccca a                                                   21

<210> SEQ ID NO 3
<211> LENGTH: 24
<212> TYPE: DNA
<213> ORGANISM: Artificial Sequence
<220> FEATURE:
<223> OTHER INFORMATION: A synthetic oligonucleotide

<400> SEQUENCE: 3
atgagcaagg gcgaggaact gttc                                                24

<210> SEQ ID NO 4
<211> LENGTH: 23
<212> TYPE: DNA
<213> ORGANISM: Artificial Sequence
<220> FEATURE:
<223> OTHER INFORMATION: A synthetic oligonucleotide

<400> SEQUENCE: 4
gtgtcacctt cgaacttgac ttc                                                 23

<210> SEQ ID NO 5
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 5
actatcccga ccgccttact                                                     20

<210> SEQ ID NO 6
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 6
ctgtagcggc tgatgttgaa                                                     20
```

```
<210> SEQ ID NO 7
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 7
ctctggccat ctgctgatcc                                               20

<210> SEQ ID NO 8
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 8
cgccgcataa ccagtgaaac                                               20

<210> SEQ ID NO 9
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 9
actacatctt gagttgcagg c                                             21

<210> SEQ ID NO 10
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 10
cctgttttgc acgttcaccg                                               20

<210> SEQ ID NO 11
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 11
cttcaggcgc gcggtctgg                                                19

<210> SEQ ID NO 12
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 12
gagacggaaa tccatcgctc                                               20

<210> SEQ ID NO 13
<211> LENGTH: 20
<212> TYPE: DNA
<213> ORGANISM: Artificial Sequence
<220> FEATURE:
<223> OTHER INFORMATION: A synthetic oligonucleotide
```

```
<400> SEQUENCE: 13
cgtactgacg gtgggagaat                                               20

<210> SEQ ID NO 14
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 14
cccggcaaaa caggtagtta                                               20

<210> SEQ ID NO 15
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 15
gttcggcttc tggcgtgt                                                 18

<210> SEQ ID NO 16
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 16
gttgcaccac agatgaaacg                                               20

<210> SEQ ID NO 17
<211> LENGTH: 18
<212> TYPE: DNA
<213> ORGANISM: Artificial Sequence
<220> FEATURE:
<223> OTHER INFORMATION: A synthetic oligonucleotide

<400> SEQUENCE: 17
gttcggcttc tggcgtgt                                                 18

<210> SEQ ID NO 18
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 18
gtaggtcagg gtggtcacga                                               20

<210> SEQ ID NO 19
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 19
tgttaccaac tgggacgaca                                               20

<210> SEQ ID NO 20
```

```
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 20 gggtgttga aggtctcaaa                                                   20

<210> SEQ ID NO 21
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 21
gccctacaga ccatgaaaca ag                                               22

<210> SEQ ID NO 22
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 22
gtgaaacaga cttcctggtc ct                                               22

<210> SEQ ID NO 23
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 23
ctccctggac ttggatggta                                                  20

<210> SEQ ID NO 24
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 24
acgctggttc ttcaaggtgt                                                  20

<210> SEQ ID NO 25
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 25
atcgagatca ccacctaccg                                                  20

<210> SEQ ID NO 26
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 26
```

```
tgaagccagg gctagtgagt                                              20

<210> SEQ ID NO 27
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 27
cgaggcactc aaggaagaac                                              20

<210> SEQ ID NO 28
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 28
gctgaggtcc tgagatttgg                                              20

<210> SEQ ID NO 29
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 29
accctcccga gattacaacc                                              20

<210> SEQ ID NO 30
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 30
caaggcgtgt tctgtctcaa                                              20

<210> SEQ ID NO 31
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 31
actgtgaagg gacggtcaac                                              20

<210> SEQ ID NO 32
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 32
ggagcagcag gatcagaatc                                              20

<210> SEQ ID NO 33
<211> LENGTH: 20
<212> TYPE: DNA
```

```
<213> ORGANISM: Artificial Sequence
<220> FEATURE:
<223> OTHER INFORMATION: A synthetic oligonucleotide

<400> SEQUENCE: 33
gctgtcattg tggtggtgtc                                                 20

<210> SEQ ID NO 34
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 34
ccctcctcag ttcagcactc                                                 20

<210> SEQ ID NO 35
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 35
tcagggagcc cattactgtc                                                 20

<210> SEQ ID NO 36
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 36
gttgtccacc atcgcttctt                                                 20

<210> SEQ ID NO 37
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 37
gaagggctat cacccaatca                                                 20

<210> SEQ ID NO 38
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 38
tgatgagctg cgaggtaatg                                                 20

<210> SEQ ID NO 39
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 39
gaagccctgg agaacctctt                                                 20
```

<210> SEQ ID NO 40
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 40
accagacctc caccttctcc                                               20

<210> SEQ ID NO 41
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 41
tacccaatcc tggactctgc                                               20

<210> SEQ ID NO 42
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 42
ggacgggttg agtttgctc                                                19

<210> SEQ ID NO 43
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 43
tgttgacaga tccccaagaa                                               20

<210> SEQ ID NO 44
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 44
ctgggcacca gtcaattaca                                               20

<210> SEQ ID NO 45
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 45
ctttatggtg tgggccaaag                                               20

<210> SEQ ID NO 46
<211> LENGTH: 20
<212> TYPE: DNA
<213> ORGANISM: Artificial Sequence
<220> FEATURE:

```
<223> OTHER INFORMATION: A synthetic oligonucleotide

<400> SEQUENCE: 46
cttctctgcc aaggtcaacg                                                  20

<210> SEQ ID NO 47
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 47
tcaaaccaga aaacggaagc                                                  20

<210> SEQ ID NO 48
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 48
gcatctcttc actgctgctg                                                  20

<210> SEQ ID NO 49
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 49
caacacagtc cccgttcttt                                                  20

<210> SEQ ID NO 50
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 50
tggtacaggc gtcaagagtg                                                  20

<210> SEQ ID NO 51
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 51
ccgcaatctc agaacctcat                                                  20

<210> SEQ ID NO 52
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 52
aggctgctag ccacactgtt                                                  20
```

```
<210> SEQ ID NO 53
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 53
acaaggatgc ctctccacac                                               20

<210> SEQ ID NO 54
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 54
acctcagcat gacatgacca                                               20

<210> SEQ ID NO 55
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 55
cccgggactt aactgtaacg                                               20

<210> SEQ ID NO 56
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 56
tcatgttgct cacggaagag                                               20

<210> SEQ ID NO 57
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 57
tctgcgaact ccttctggat                                               20

<210> SEQ ID NO 58
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 58
ccgagggacg atgtagtcat                                               20

<210> SEQ ID NO 59
<211> LENGTH: 20
<212> TYPE: DNA
<213> ORGANISM: Artificial Sequence
<220> FEATURE:
<223> OTHER INFORMATION: A synthetic oligonucleotide
```

```
<400> SEQUENCE: 59
ccctggagca aactcaagtc                                              20

<210> SEQ ID NO 60
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 60
ttggacggac gcttattttc                                              20

<210> SEQ ID NO 61
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 61
aacttaacct aggcgtcgca                                              20

<210> SEQ ID NO 62
<211> LENGTH: 21
<212> TYPE: DNA
<213> ORGANISM: Artificial Sequence
<220> FEATURE:
<223> OTHER INFORMATION: A synthetic oligonucleotide

<400> SEQUENCE: 62
cattcgcttg gcatcagaag c                                            21

<210> SEQ ID NO 63
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 63
acttggcagg accagagaga                                              20

<210> SEQ ID NO 64
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 64
agagttcggg tccagaggtt                                              20

<210> SEQ ID NO 65
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 65
gacccacaag tggcacaac                                               19

<210> SEQ ID NO 66
<211> LENGTH: 20
```

```
<212> TYPE: DNA
<213> ORGANISM: Artificial Sequence
<220> FEATURE:
<223> OTHER INFORMATION: A synthetic oligonucleotide

<400> SEQUENCE: 66
tctacaatgc cacgcttctg                                               20

<210> SEQ ID NO 67
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 67
aggctgagaa ctctcgcttg                                               20

<210> SEQ ID NO 68
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 68
attaggcaag ggggaagaga                                               20

<210> SEQ ID NO 69
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 69
atgcttctct ggcacgtctt                                               20

<210> SEQ ID NO 70
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 70
agccacgctt tcatactgct                                               20

<210> SEQ ID NO 71
<211> LENGTH: 19
<212> TYPE: DNA
<213> ORGANISM: Artificial Sequence
<220> FEATURE:
<223> OTHER INFORMATION: A synthetic oligonucleotide

<400> SEQUENCE: 71
ctttgcctct gggaagacc                                                19

<210> SEQ ID NO 72
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 72
```
cagagtcgtt ggctgtgaaa                                                   20

<210> SEQ ID NO 73
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 73
gacaaggaaa gctgcctgac                                                   20

<210> SEQ ID NO 74
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 74
ttctgcaaag tcagcattgg                                                   20

<210> SEQ ID NO 75
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 75
acctctttgg agctgggttt                                                   20

<210> SEQ ID NO 76
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 76
gatagggcag ctgaggtctg                                                   20

<210> SEQ ID NO 77
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 77
ctggccacca tgaaagagtt                                                   20

<210> SEQ ID NO 78
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 78
gggctccctg gtatttcttc                                                   20

<210> SEQ ID NO 79
<211> LENGTH: 20
<212> TYPE: DNA
<213> ORGANISM: Artificial Sequence

```
<220> FEATURE:
<223> OTHER INFORMATION: A synthetic oligonucleotide

<400> SEQUENCE: 79
tgaaaagcag ctgatggatg                                               20

<210> SEQ ID NO 80
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 80
aatacccgtg gaatgctctg                                               20

<210> SEQ ID NO 81
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 81
cgatcactac tgggatttct cc                                            22

<210> SEQ ID NO 82
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 82
caaggtttga taagggaagc ac                                            22

<210> SEQ ID NO 83
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 83
tactacaagc tgggacggaa at                                            22

<210> SEQ ID NO 84
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 84
atgtcggagt tgatgagaag gt                                            22

<210> SEQ ID NO 85
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 85
ggagatttct gatggtcctc ac                                            22
```

```
<210> SEQ ID NO 86
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 86
agtaacttgg ccaggaaatt ga                                              22

<210> SEQ ID NO 87
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 87
ttcagatgtg catcgtgtca                                                 20

<210> SEQ ID NO 88
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 88
ccagcggtta ggcttcatac                                                 20

<210> SEQ ID NO 89
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 89
caggatgggt ggaacatact ct                                              22

<210> SEQ ID NO 90
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 90
cattttgctc tccaaacaaa ca                                              22

<210> SEQ ID NO 91
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 91
tcctgcccac catctacttc                                                 20

<210> SEQ ID NO 92
<211> LENGTH: 20
<212> TYPE: DNA
<213> ORGANISM: Artificial Sequence
<220> FEATURE:
<223> OTHER INFORMATION: A synthetic oligonucleotide
```

```
<400> SEQUENCE: 92
ccgtcatgct ccttagcttc                                                  20

<210> SEQ ID NO 93
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 93
atattgtggc cggagctata aa                                               22

<210> SEQ ID NO 94
<211> LENGTH: 22
<212> TYPE: DNA
<213> ORGANISM: Artificial Sequence
<220> FEATURE:
<223> OTHER INFORMATION: A synthetic oligonucleotide

<400> SEQUENCE: 94
gctcctatct tgcacaggtc tt                                               22

<210> SEQ ID NO 95
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 95
tgggagtttc ccagaaacag                                                  20

<210> SEQ ID NO 96
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 96
aaatgggcac ttggtttgag                                                  20

<210> SEQ ID NO 97
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 97
agtctgctga agaggccttg                                                  20

<210> SEQ ID NO 98
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 98
aacgcaacta gggtgtacgg                                                  20

<210> SEQ ID NO 99
```

```
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 99
taaaggctca ggctggtgtt                                           20

<210> SEQ ID NO 100
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 100
tggagagcaa accaaccaat                                           20

<210> SEQ ID NO 101
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 101
ccacttgcca caacaacatc                                           20

<210> SEQ ID NO 102
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 102
tggactcaca ggagcaagtg                                           20

<210> SEQ ID NO 103
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 103
cttcaagctg ccagaaaacc                                           20

<210> SEQ ID NO 104
<211> LENGTH: 20
<212> TYPE: DNA
<213> ORGANISM: Artificial Sequence
<220> FEATURE:
<223> OTHER INFORMATION: A synthetic oligonucleotide

<400> SEQUENCE: 104
attcggaaga attggcctct                                           20
```

ENDODERMAL PROGENITOR CELLS

RELATED APPLICATION

This application is a national stage application under 35 U.S.C. §371 of PCT/US2007/024415, filed Nov. 26, 2007, and published as WO 2008/063675A3 on May 29, 2008, which claims priority from U.S. Provisional Application Ser. No. 60/867,135 filed Nov. 24, 2006, which applications and publication are herein incorporated by reference in their entirety.

STATEMENT OF GOVERNMENT RIGHTS

This invention was made with the assistance of government support under United States Grant Nos. R01-HL073221 and U19 DK61244 from the National Institutes of Health. The government may have certain rights in the invention.

FIELD OF THE INVENTION

This invention relates to the field of progenitor cells obtained from endodermal tissues and methods of isolation, culture, differentiation and use thereof.

BACKGROUND OF THE INVENTION

Type-1 diabetes (T1DM) is an autoimmune disorder which results in the selective destruction of more than 80% of endogenous insulin producing beta-cells (Pipeleers and Ling 1992). This disease most often appears during childhood or adolescence and is characterized by insulin deficiency, abrupt onset of symptoms, proneness to ketosis, and exogenous insulin dependency (Pociot and McDermott 2002). It is estimated that as many as three million people in the U.S. suffer from T1DM (Juvenile Diabetes Research Foundation, 2004).

Although exogenous insulin delivery has remained a suitable remedy for most T1DM patients, some individuals continually suffer from uncontrollable blood glucose-levels, leading to disease-related complications including blindness, neuropathy, nephropathy, myocardial infarction, stroke, and limb ischemia (Brownlee 2001). Over the last decade, islet transplantation has arisen as a potential alternative therapy for T1DM. Although islet-transplantation holds great promise, the scarcity of donor tissue makes such therapy available to <0.5% of potential transplant recipients.

A recent study has suggested that beta cells in the normal and regenerating adult murine pancreas are formed by self-duplication rather than contribution from a stem/progenitor cell (Dor et al. 2004). This data suggests a regenerative mechanism in the pancreas much like that described for the liver (Michalopoulos and DeFrances 1997). Under steady state conditions to moderate damage (damage ≤⅔ cellular mass), hepatocytes proliferate as a means to replace damaged cells (Michalopoulos and DeFrances 1997; Oh et al. 2002). It is not until this hepatic damage is followed by inhibition of hepatocyte proliferation (i.e., 2-AAF treatment), or severe loss of hepatocytes (90%), that a population of liver progenitor cells (termed oval cells) becomes activated and serves as a precursor for mature hepatocytes (Oh et al. 2002). Oval cells in the liver are bipotential progenitor cells, capable of giving rise to both hepatocytes and bile duct cells (Oh et al. 2002; Knight et al. 2005). Although not as extensively studied, oval cells have also been observed in the pancreas of rats and mice fed a copper-deficient diet (Ide et al. 1993; Jeffers et al. 1996). Phenotypically, mouse liver oval cells have been described as expressing numerous epithelial and hematopoietic markers including alpha fetoprotein (Afp), cMet, cytokeratins (CKs) 7, 8, 18, 19, CD34, CD45, Sca1, and Thy1 (Knight et al. 2005; Jeffers et al. 1996; Petersen et al. 2003; Petersen et al. 1998).

Cellular therapy with stem cells and their progeny is a promising medical treatment. Pancreatic islet transplantation provides a viable method for repopulation of pancreatic tissues damaged by disease or loss of pancreatic mass; however, current methods for culturing and maintenance of primary pancreatic culture are not sufficient for successful transplantation. Isolation and maintenance of pancreatic oval cells requires the addition of chemicals or other exogenous stressors (e.g., in vivo) for their proliferation making the cells less useful clinically (Jeffers et al. 1996; Petersen et al. 2003; Petersen et al. 1998; Wang et al. 2003; Rao and Reddy 1991). Therefore, a need exists to identify, isolate and characterize primitive cells that can differentiate into viable endodermal tissue, such as pancreatic tissue, and can be used in cellular replacement therapies, as well as to develop methods for isolating and culturing such cells without the need for the addition of chemicals or other exogenous stressors that may reduce the clinical applications of such cells.

SUMMARY OF THE INVENTION

The present invention provides for the isolation of endodermal progenitor cells from tissue, such as endodermal tissue, including pancreas, which has not been subjected to an exogenous stressor (e.g., in vivo). Methods of the invention can result in the isolation of a population of progenitor cells that have a different phenotype from other previously identified progenitor cells. Therefore, the present invention relates to a progenitor cell and methods of isolation, culture, differentiation and use thereof.

One embodiment provides a method of obtaining endodermal progenitor cells comprising: (a) culturing a cell population obtained from a tissue to induce cluster formation in culture medium; (b) culturing the clusters in culture medium; and (c) isolating endodermal progenitor cells, wherein the function of a cell in the tissue is not reduced by application of an exogenous stressor prior to harvesting the tissue (e.g., the tissue has not been subject to any stressor while in vivo, including, but not limited to, physical manipulation, exposure to toxins or other agents, or subject to stress, such as nutritional stress (e.g., copper depletion diet) prior to harvesting).

In one embodiment, the tissue is endodermal tissue. For example, in one embodiment, the endodermal tissue is derived from the group consisting of liver, stomach, intestine, pancreas, lung, colon, bladder or thyroid. In one embodiment, the cell population can be enriched or unfractionated (e.g., for pancreas, one can use an islet enriched fraction or unfractionated pancreas).

In another embodiment, the clusters are isolated prior to culturing in step (b). In one embodiment, the clusters of step (b) are cultured with one or more attachment factors, including, but not limited to, one or more of collagen type I, collagen type II, collagen type IV, fibronectin, chondroitin sulfate, vitronectin, thrombospondin, or matrigel.

In one embodiment, the culture medium of step (b) is changed (e.g., replaced by fresh media) every two to three days for at least about 7 days. In another embodiment, after about 7 days the culture medium of step (b) is not changed prior to isolating the endodermal progenitor cells from the cultured population.

In one embodiment, the culture medium of step (a) and/or (b) comprises serum (e.g., about 0.5% to about 5% serum). In one embodiment, the culture medium of step (a) and/or (b) comprises one or more of EGF, LIF, basic FGF, or PDGF.

In one embodiment, the cell population is subjected to continuous density gradient centrifugation prior to step (a). In another embodiment, the tissue is dissociated (e.g., mechanically or chemically (e.g., enzymatically) so as to allow cells to dissociate from the tissue which cells can then be cultured so as to form clusters) prior to step (a).

In one embodiment, the endodermal tissue is disassociated enzymatically (e.g., by one or more of collagenase, trypsin, dispase I, hyaluronidase, thermolysin, neutral protease, liberase RI, DNase I, pancreatin, pronase or combination thereof). In one embodiment, the enzyme does not adversely effect the viability of the cell or enrich for a specific cell type.

In one embodiment, the tissue is obtained from a mammal (e.g., human, swine, rat or mouse, such as one which is free of diseases of the tissue of interest (e.g., liver disease (hepatitis), diabetes).

One embodiment provides an endodermal progenitor cell prepared by the methods described herein. In one embodiment, the progenitor cell originates in the bone marrow. Another embodiment provides a composition (e.g., a pharmaceutical and/or cell culture composition) comprising a population of endodermal progenitor cells. In embodiment, the composition comprises a carrier (e.g., a pharmaceutically acceptable carrier and/or cell culture medium).

One embodiment provides a method for differentiating the endodermal progenitor cells to yield an endodermal cell type (e.g., a cell type further differentiated than the endodermal progenitor cell, such as a cell that is committed to a particular endodermal cell type, including pancreatic, islet, intestinal, thyroid, lung, colon, bladder or liver cell types).

In one embodiment, the endodermal progenitor cells are differentiated (ex vivo or in vivo) in the presence of one or more differentiation factors comprising one or more of β-cellulin, GLP-1, HGF, FGF, EGF, KGF, nicotinamide, TGF-α, TGF-β, activin, cyclopamin, BMP4, an SHH antibody, FGF, EGF, oncostatin M, dexamethasone, exendin4, GDF11, or nicotinamide.

One embodiment provides a method for providing an endoderm cell type to a subject in need thereof, comprising administering to the subject an endodermal progenitor cell described herein or differentiated progeny derived therefrom in an amount effective to provide an endoderm cell type to the subject. Another embodiment provides a method wherein the endodermal progenitor cells or differentiated progeny thereof are administered by contacting the cells with a damaged tissue of the subject, such as a damaged liver or pancreas, but can also be contacted with normal tissues. An effective amount of endodermal progenitor cells or differentiated progeny therefrom can be administered to a subject by systemic or localized injection, catheterized delivery and/or topical application.

One embodiment provides for use of endodermal progenitor cells in medical therapy. The medical therapy includes treating pancreatic, intestinal, thyroid, lung, bladder or liver damage as a result of an injury or disease. Another embodiment provides the use of endodermal progenitor cells to prepare a medicament for treating pancreatic, intestinal, thyroid, lung, bladder, or liver damage as a result of injury or disease. The medicament may also include a physiologically acceptable carrier and/or cell culture medium.

BRIEF DESCRIPTION OF THE DRAWINGS

FIG. 1 depicts the PCR primers used for real-time RT-qPCR.

FIG. 8. Bone marrow cells do not acquire PDPC characteristics by coculture with pancreatic cells. GFP+Sca1+ BM cells were spiked into day 7 PDPC cultures initiated with pancreata from wild-type animals. (A) 7 days later, GFP positive cells were present throughout apparent PDPC colonies as demonstrated by fluorescence microscopy. (B) Cells were harvested on day 14 of culture, stained with anti-CD45 antibodies and analyzed by FACS. (C) GFP+CD45+ cells were sorted by FACS (B-b, c) and analyzed by real-time RT-qRT-PCR for CK7, CK8, CK18, CK19 and Afp in comparison with levels in freshly isolated Sca1+ BM cells. Expression relative to fresh Sca1+ cells and CD45+ PDPCs is shown.

DETAILED DESCRIPTION OF THE INVENTION

Definitions

Figure 2:
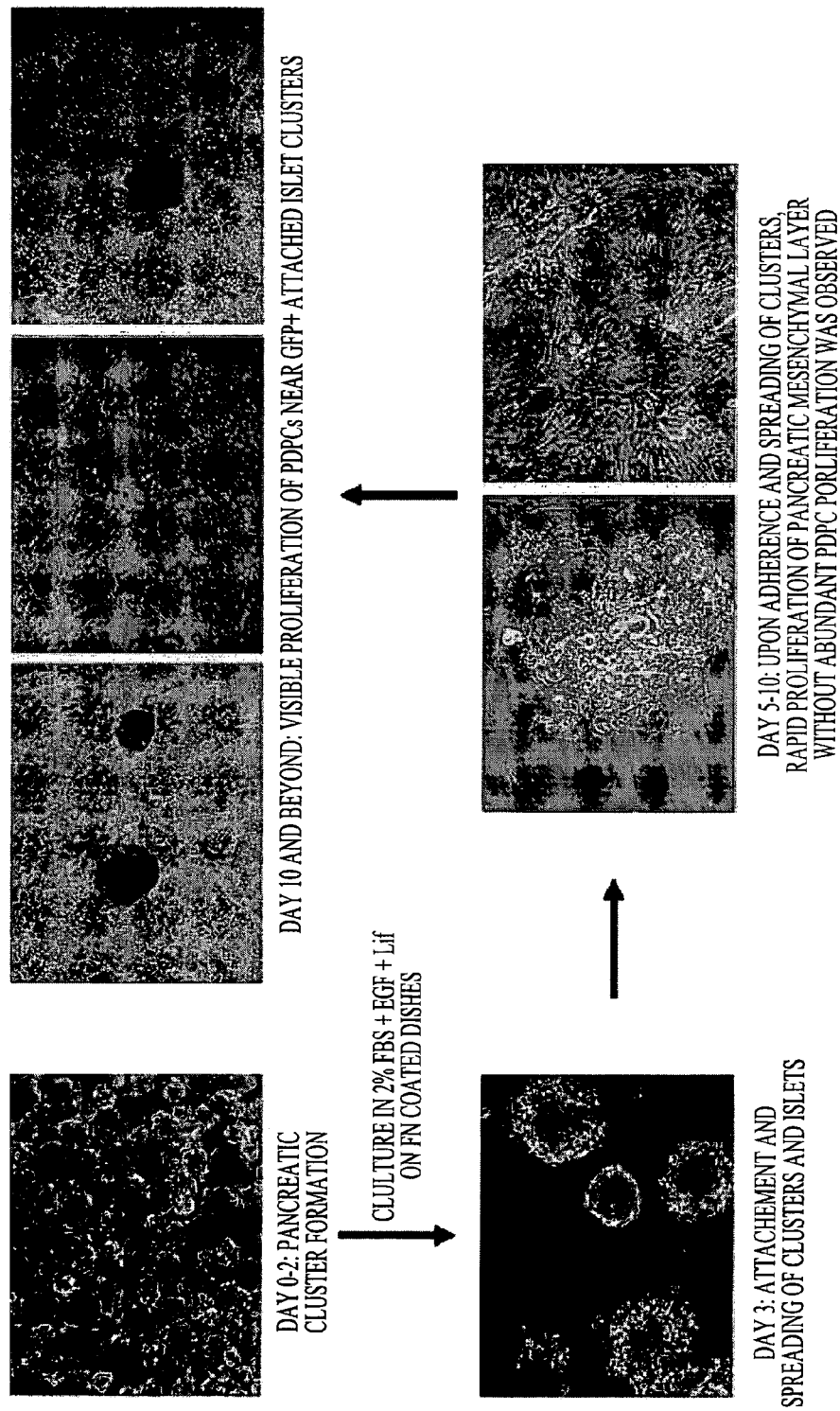
FIG. 2 depicts the emergence of endodermal progenitor cells in culture initiated with islet-enriched preparations from Pdx-1-GFP mice. After cluster attachment, endodermal cells spread, followed by the proliferation of mesenchymal cells (d5-10), and subsequent proliferation of pancreas-derived progenitor cells (PDPCs) surrounding attached islet clusters (green=Pdx1-GFP). Representative example of >50 isolations.

As used herein, the terms below are defined by the following meanings:

" Endodermal progenitor cells," "Pancreas-derived endodermal progenitor cells," "Pancreas-derived $_p$rogenitor cells" or "PDPCs" are cells isolated from an endodermal tissue (e.g., pancreas) that can differentiate into more than one endodermal cell type (such cells may also be able to differentiated into cells of more than one embryonic layer (e.g., endodermal, mesodermal, and/or ectodermal)).

The term "isolated" refers to a cell or cells which are not associated with one or more cells or one or more cellular components that are associated with the cell or cells in vivo.

A "cluster" of cells is defined herein as a multi-cellular aggregate consisting of more than a single cell (e.g., when cultured in suspension) that has initially developed from a single or from multiple cells. For example, a cluster of cells is an aggregate of more than one cell, including two or more cells, about 5 cells, about 10 cells, about 20 cells, about 25 cells, about 30 cells, about 35 cells, about 40 cells, about 50 cells, about 60 cells, about 70 cells, about 80 cells, about 90 cells about 100 cells, about 150 cells, about 200 cells and so on (e.g., a cluster of cells can include an aggregate of cells comprising about 10 to about 100 cells or about 50 to about 1000 cells or greater). Clusters can be grown adherently or in suspension.

A "subject" is a vertebrate, such as a mammal, including a human. Mammals include, but are not limited to, humans, farm animals, sport animals and companion animals. Included in the term "animal" is dog, cat, fish, gerbil, guinea pig, hamster, horse, rabbit, swine, mouse, monkey (e.g., ape, gorilla, chimpanzee, orangutan) rat, sheep, goat, cow and bird. Subjects that can benefit from the cells and methods of the invention include, but are not limited to, those suffering from a loss of function of endodermal cells, including, but not limited to, liver or pancreatic cells, as a result of physical or disease related damage.

An "effective amount" generally means an amount which provides the desired local or systemic effect and/or performance, particularly for treating a condition of interest.

The terms "comprises," "comprising," and the like can have the meaning ascribed to them in U.S. Patent Law and can mean "includes," "including" and the like. As used herein, "including" or "includes" or the like means including, without limitation.

Isolation and Characterization of Pancreas-Derived Endodermal Progenitor Cells

The present invention relates to endodermal progenitor cells and methods of isolation, culture, differentiation and use thereof. Unlike traditional isolation and culture protocols for liver or pancreatic oval cells, methods of the present invention require no exogenous stressor (e.g., reduction of cell mass and/or function) to the endodermal tissue prior to or during harvesting of the endodermal tissue. As used herein, an "exogenous stressor," includes adverse chemicals (e.g., those which render a cell preparation unsuitable for clinical use), toxins (e.g., N-2-acetylaminofluorene, 3,5-diethoxycarbony-1.4-dihydrocollidine, streptozotocin), nutritional stressors (e.g., diets deficient in one or more nutrients or diets supplemented with an agent (e.g., an agent that effects cell function or alters cell environment)), cell depletion, or physical stress. For example, the subject/endodermal tissue, such as liver or pancreas, has not been manipulated/exposed to surgical resection, pancreatectomy (e.g., partial), pancreatic duct ligation, nutritional stress (e.g., copper depleted diet, choline-deficient diet), or necrosis/atrophy, chemically induced or otherwise, prior to harvesting of the endodermal tissue, or harvesting conditions designed to destroy cells (e.g., hepatocytes). (Preferably the enzymes used during harvesting do not adversely effect the viability of the cell or enrich or select for a specific cell type.) For example, prior to harvesting, pancreatic tissue is not depleted (a reduction) of acinar tissue or cells. Frequently, cells isolated by protocols with exogenous stressors transform into a tumorigenic phenotype due to treatment agents etc., precluding their use for clinical application.

In one embodiment, the endodermal tissue has not been manipulated so as to stimulate endodermal tissue growth and/or inhibit cell growth, for example, inhibit normal mechanisms for liver growth restoration, such as by exposure to toxins, for example, those toxins and/or agents which inhibit mature cells, including but not limited to, hepatocytes. For example, the endodermal tissue, such as liver or pancreas, is not manipulated to generate concurrent stimulation of growth and inhibition of normal mechanisms for tissue growth (i.e., blockade of proliferation of hepatocytes). For example, the stimulus for tissue growth can be satisfied through different methods, including surgical resection, nutritional stress, or chemically induced necrosis. Blockade of proliferation is frequently achieved using chemicals (such as 2-acetylaminofluorene and various carcinogens) that impede or prevent mitotic division of mature endodermal cells (e.g., hepatocytes).

Methods of isolating endodermal progenitor cells are provided including disassociating an endodermal tissue to form a heterogeneous population of primary cells (e.g., pancreatic cells); culturing the primary cell population in liquid culture medium so that cells in the primary cell population form clusters;

culturing the clusters in culture medium in the presence of one or more attachment factors and isolating the endodermal progenitor cells.

Starting material for the culture system comprises heterogeneous populations of primary endodermal cells which can be obtained according to any method available to the art, including, but not limited to, enzymatic degradation, mechanical separation, filtration, centrifugation (e.g., continuous density gradient (e.g., sucrose, Percoll, or Ficoll Hypaque) centrifugation, differential centrifugation) and combinations thereof. Additionally, immunomagnetic beads can also be used to selectively separate cell populations of interest based on cell-surface marker expression. The endodermal tissue can be obtained from a mammal, such as rat, mouse, pig or human.

The number and quality of the isolated endodermal cells can vary depending on the quality of the tissue used, the composition of solutions, and the type and concentration of enzyme. Frequently used enzymes include, but are not limited to, collagenase, pronase, trypsin, dispase I, hyaluronidase, thermolysin, neutral protease, liberase RI, DNase I, pancreatin or a combination thereof.

One embodiment provides a method of isolating a population of endodermal progenitor cells comprising: (a) disassociating harvested endodermal tissue to form a heterogeneous population of primary endodermal cells; (b) culturing the primary cell population in culture medium so as to induce cluster formation; (c) culturing the clusters in culture medium in the presence of one or more attachment factors; and (d) isolating endodermal progenitor cells, wherein the endodermal tissue is not subject to an exogenous stressor prior to harvesting. In one embodiment, the primary endodermal cells are subjected to continuous density gradient centrifugation prior to step (b). In one embodiment, the culturing of step (c) is extended for about 5 to about 7 days or greater, such as about 7 to about 14 days, or about 10 to about 14 days. Cultures can be extended for durations beyond 14 days, such as about 15 to about 20 days and even longer, for about 21 to about 28 days, where desired.

The cells can also be isolated in the presence of various factors such as LIF (e.g., at a concentration of about 5,000 U/ml to about 50,000 U/ml, such as about 10,000 U/ml), EGF (e.g., at a concentration of about 5 ng/ml to about 50 ng/ml, such as about 10 ng/ml), basic FGF (e.g., at a concentration of about 5 ng/ml to about 50 ng/ml, such as about 10 ng/ml) or PDGF (e.g., at a concentration of about 5 ng/ml to about 50 ng/ml, such as about 10 ng/ml).

During and after isolation, the endodermal progenitor cells of the invention can be cultured in culture medium that is well established in the art and commercially available from the American Type Culture Collection (ATCC). Such media include, but are not limited to, Dulbecco's Modified Eagle's Medium (DMEM), DMEM F12 medium, Eagle's Minimum Essential Medium, F-12K medium, Iscove's Modified Dulbecco's Medium, or RPMI-1640 medium. It is within the skill of one in the art to modify or modulate concentrations of media and/or media supplements as needed for the cells used. It will also be apparent that many media are available as low-glucose formulations, with or without sodium pyruvate.

Also contemplated is supplementation of cell culture medium with mammalian sera. Sera often contain cellular factors and components that are necessary for viability and expansion. Examples of sera include fetal bovine serum (FBS), bovine serum (BS), calf serum (CS), fetal calf serum (FCS), newborn calf serum (NCS), goat serum (GS), horse serum (HS), human serum, chicken serum, porcine serum, sheep serum, rabbit serum, rat serum (RS), serum replacements, and bovine embryonic fluid. It is understood that sera can be heat-inactivated at 55-65° C. if deemed necessary to inactivate components of the complement cascade. Modulation of serum concentrations, or withdrawal of serum from the culture medium can also be used to promote survival of one or more desired cell types. In one embodiment, the endodermal progenitor cells are cultured in the presence of FBS for serum specific for the species cell type. For example, endodermal progenitor cells can be isolated and/or expanded with total serum (e.g., FBS) concentrations of about 0.5% to about 5% or greater including about 5% to about 15%. Concentrations of serum can be determined empirically.

Additional supplements can also be used to supply the cells with trace elements for optimal growth and expansion. Such supplements include insulin, transferrin, sodium selenium, and combinations thereof. These components can be included in a salt solution such as, but not limited to, Hanks' Balanced Salt Solution® (HBSS), Earle's Salt Solution®, antioxidant supplements, MCDB-201® supplements, phosphate buffered saline (PBS), N-2-hydroxyethylpiperazine-N'-ethanesulfonic acid (HEPES), nicotinamide, ascorbic acid and/or ascorbic acid-2-phosphate, as well as additional amino acids. Many cell culture media already contain amino acids; however some require supplementation prior to culturing cells. Such amino acids include, but are not limited to, L-alanine, L-arginine, L-aspartic acid, L-asparagine, L-cysteine, L-cystine, L-glutamic acid, L-glutamine, L-glycine, L-histidine, L-inositol, L-isoleucine, L-leucine, L-lysine, L-methionine, L-phenylalanine, L-proline, L-serine, L-threonine, L-tryptophan, L-tyrosine, and L-valine.

Antibiotics are also typically used in cell culture to mitigate bacterial, mycoplasmal, and fungal contamination. Typically, antibiotics or anti-mycotic compounds used are mixtures of penicillin/streptomycin, but can also include, but are not limited to, amphotericin (Fungizone®), ampicillin, gentamicin, bleomycin, hygromycin, kanamycin, mitomycin, mycophenolic acid, nalidixic acid, neomycin, nystatin, paromomycin, polymyxin, puromycin, rifampicin, spectinomycin, tetracycline, tylosin, and zeocin.

Hormones can also be advantageously used in cell culture and include, but are not limited to, D-aldosterone, diethylstilbestrol (DES), dexamethasone, β-estradiol, hydrocortisone, insulin, prolactin, progesterone, somatostatin/human growth hormone (HGH), thyrotropin, thyroxine, and L-thyronine. β-mercaptoethanol can also be supplemented in cell culture media.

Lipids and lipid carriers can also be used to supplement cell culture media, depending on the type of cell and the fate of the differentiated cell. Such lipids and carriers can include, but are not limited to cyclodextrin (α, β, γ), cholesterol, linoleic acid conjugated to albumin, linoleic acid and oleic acid conjugated to albumin, unconjugated linoleic acid, linoleic-oleic-arachidonic acid conjugated to albumin, oleic acid unconjugated and conjugated to albumin, among others. Albumin can similarly be used in fatty-acid free formulation.

Also contemplated is the use of feeder cell layers. Feeder cells are used to support the growth of fastidious cultured cells, including pancreas-derived endodermal progenitor cells. Feeder cells are normal cells that have been inactivated by γ-irradiation. In culture, the feeder layer serves as a basal layer for other cells and supplies cellular factors without further growth or division of their own (Lim and Bodnar 2002). Examples of feeder layer cells typically used with liver cell cultures are hepatocytes and embryonic fibroblasts (Suzuki, A. et al. 2000), but can be any post-mitotic cell that is capable of supplying cellular components and factors that are advantageous in allowing optimal growth, viability, and expansion of endodermal progenitor cells. In some cases, feeder cell layers are not needed to keep cells in an undifferentiated, proliferative state, as leukemia inhibitory factor (LIF) has anti-differentiation properties. Often, supplementation of a defined concentration of LIF is all that is necessary to maintain cells in an undifferentiated state.

Cells in culture can be maintained either in suspension or attached to a solid support, such as extracellular matrix components and synthetic or biopolymers. Cells often require additional factors that encourage their attachment to a solid support (e.g., attachment factors) such as type I, type II, and type IV collagen, concanavalin A, chondroitin sulfate, fibronectin, "superfibronectin" and/or fibronectin-like polymers, gelatin, laminin, poly-D and poly-L-lysine, Matrigel™, thrombospondin, and/or vitronectin.

The maintenance conditions of cells can also contain cellular factors that allow cells, such as the endodermal progenitor cells of the invention, to remain in an undifferentiated form. It may be advantageous under conditions where the cell must remain in an undifferentiated state of self-renewal for the medium to contain epidermal growth factor (EGF), platelet derived growth factor (PDGF), leukemia inhibitory factor (LIF), basic fibroblast growth factor (bFGF) and combinations thereof. It is apparent to those skilled in the art that supplements that allow the cell to self-renew (e.g., to produce replicate daughter cells having differentiation potential that is identical to those from which they arose; a similar term used in this context is "proliferation"), but not differentiate should be removed from the culture medium prior to differentiation. It is also apparent that not all cells will require these factors. In fact, these factors may elicit unwanted effects, depending on the cell type.

Endodermal progenitor cells can be selected based on the markers (gene and/or protein) described herein. Accordingly, positive selection methods can be used, either alone or together with the methods described above, to identify and/or isolate the cells of the invention. Methods of positive selection can include visual selection, using microscopy and/or other means of detection, including, but not limited to, immunoblotting, immunofluorescence, and/or enzyme-linked immunosorbent assay. Other methods of positive selection can also include, but are not limited to, additional selective culture techniques (e.g., variable cell densities or amounts of $CO_2$), flow cytometry, RT-PCR, and/or microchip-based methods of cell separation.

Uses for Endodermal Progenitor Cells

Endodermal progenitor cells can be used for the generation of endodermal lineages, including but not limited to, liver, pancreas, islet cells, lung, intestine, colon, thyroid, bladder and stomach. For example, liver cells, including hepatocytes and biliary epithelium and pancreatic cells, including acinar cells, ductal cells, islet cells, such as $\alpha$-cells, $\beta$-cells, $\delta$-cells, can be generated from the endodermal progenitor cells described herein. Stomach cells that can be generated include, but are not limited to, mucosal cells, parietal cells, chief cells, and gastric endocrine cells. Intestinal cells that can be generated, include, but are not limited to, epithelial cells and enteroendocrine cells. Thyroid cells, such as, but not limited to, follicular and parafollicular cells can be generated from the endodermal progenitor cells of the present invention. Additionally, lung cells, such as mucosal cells of the airways, which include ciliary epithelium, mucosal cells, serous cells, and alveolar cells, such as those that produce surfactants can be generated from the endodermal progenitor cells of the present invention.

Therefore, one embodiment provides methods for providing epithelial cells, which can include, but are not limited to, liver epithelial cells, biliary ductal epithelial cells, lung epithelial cells, gastric epithelial cells, or bowel epithelial cells, comprising differentiating endodermal progenitor cells in the presence of differentiation factors and isolating the epithelial cells. The differentiation factors can be, but are not limited to, HGF, FGF, TGF$\alpha$, TGF$\beta$, EGF, Oncostatin M, dexamethasone, and/or nicotinamide. Differentiation can occur in vivo or ex vivo.

The invention further provides methods for providing endodermal cells, which can be, but are not limited to, exocrine pancreatic, endocrine pancreatic, islet, thyroid, intestinal, colon, bladder and/or lung cells. The endodermal progenitor cells of the invention are differentiated in the presence of differentiation factors including, but not limited to, $\beta$-cellulin, GLP-1, HGF, KGF, nicotinamide, FGF, FGF-4, TGF-$\alpha$, TGF-$\beta$, activin, cyclopamin, and/or BMP inhibitors, and the differentiation can occur in vivo or ex vivo.

Endodermal progenitor cells of the invention can be induced to differentiate into one or more liver cell types in the presence of cytokines and growth factors, which can be liver-specific (Michalopoulos and DeFrances 1997). For example, the endodermal progenitor cells can be induced to differentiate into hepatocytes. Hepatocyte growth factor (HGF), or scatter factor, is a well-known cytokine that promotes differentiation to a hepatocyte phenotype. Similarly, epidermal growth factor (EGF) has also been implicated in proliferation and differentiation of liver cells. Other cytokines commonly associated with hepatic differentiation and proliferation are tumor necrosis factor-$\alpha$ (TNF$\alpha$), transforming growth factor-$\alpha$ (TGF-$\alpha$), insulin, IGF-1 and -2, the interleukins, such as but not limited, to IL-4, IL-6, IL-8, IL-9, and IL-13, chemokines, such as macrophage inflammatory protein (MIP-1$\alpha$, MIP-1$\beta$), RANTES, monocyte chemoattractant protein-1 (MCP-1), the GRO family, platelet derived growth factor (PDGF), keratinocyte growth factor (KGF), fibroblast growth factor-1, -2, and -4 (FGF), and norepinephrine (Leffert, H. L. et al, (1988)). Endodermal progenitor cells can be differentiated in the presence of HGF and/or FGF-4, but can also include beta-cellulin, GLP-1, HGF, KGF, nicotinamide, TGF-$\alpha$, TGF-$\beta$, activin, cyclopamin, and BMP inhibitors, among others.

Endodermal progenitor cells and other fastidious cells can benefit from co-culturing with another cell type. Such co-culturing methods arise from the observation that certain cells can supply yet-unidentified cellular factors that allow the stem cell to differentiate into a specific lineage or cell type. These cellular factors can also induce expression of cell-surface receptors, some of which can be readily identified by monoclonal antibodies. Generally, cells for co-culturing can be selected based on the type of lineage one skilled in the art wishes to induce, and it is within the abilities of the skilled artisan to select the appropriate cells for co-culture.

Methods of identifying and subsequently isolating differentiated cells from their undifferentiated counterparts can be carried out by methods well known in the art. Cells that have been induced to differentiate can be identified by selectively culturing cells under conditions whereby differentiated cells outnumber undifferentiated cells. These conditions include, for example, extending the amount of time that cells are grown in culture, such that survival of a desired cell type is encouraged. Many primary cells achieve senescence, and fail to divide, or die, after a period of time. Other conditions comprise modulating the type and concentration of serum, or culturing the cells in the presence or absence of growth factors and/or cytokines that induce differentiation to another cell type. Differentiation can also be advantageously achieved by modulation of serum concentrations, or withdrawal of serum from the culture. Other methods of inducing differentiation can include, but are not limited to, modulating the acidity of the culture medium, as well as the oxygen and carbon dioxide levels during culture.

Similarly, differentiated cells can be identified by morphological changes and characteristics that are not present on their undifferentiated counterparts, such as cell size, the number of cellular processes (i.e., formation of dendrites and/or branches), and the complexity of intracellular organelle distribution. Also contemplated are methods of identifying differentiated cells by their expression of specific cell-surface markers such as cellular receptors and transmembrane proteins. Monoclonal antibodies against these cell-surface markers can be used to identify differentiated cells. Detection of these cells can be achieved through fluorescence activated cell sorting (FACS), and/or enzyme-linked immunosorbent assay (ELISA). From the standpoint of transcriptional upregulation of specific genes, differentiated cells often display levels of gene expression that are different from undifferentiated cells. Reverse-transcription polymerase chain reaction (RT-PCR) can also be used to monitor changes in gene expression in response to differentiation. In addition, whole genome analysis using microarray technology can be used to identify differentiated cells.

Accordingly, once differentiated cells are identified, they can be separated from their undifferentiated counterparts, if necessary. The methods of identification detailed above also provide methods of separation, such as FACS, preferential cell culture methods, ELISA, magnetic beads, and combinations thereof. One embodiment of the invention envisions the use of FACS to identify and separate cells based on cell-surface antigen expression. It is understood that the methods of identification and separation are not limited to analysis of differentiated cell types, but can also be used to identify undifferentiated cell types such as the endodermal progenitor cells of the invention.

Endodermal progenitor cells of the invention can also be used in cell replacement therapies. Endodermal progenitor cells can be administered to a tissue of interest in a subject to supplement functioning cells or replace cells, which have lost function. Alternatively, methods of providing differentiated cells are also contemplated, wherein the endodermal progenitor cells are differentiated in the presence of differentiation factors, isolated, and administered into or upon the body of a subject. In one embodiment, the differentiated cells are cells of the endodermal lineage, such as pancreas cells (e.g., beta cells).

Disease states characterized by loss of liver mass and/or function, and that could benefit from endodermal progenitor cells and methods of the invention include, but are not limited to, Alagille Syndrome, alcoholic liver disease (alcohol-induced cirrhosis), α-1-antitrypsin deficiency, autoimmune hepatitis, Budd-Chiari Syndrome, biliary atresia, Byler Disease, cancer of the liver, Caroli Disease, Brigler-Najjar Syndrome, Dubin-Johnson Syndrome, fatty liver, galactosemia, Gilbert Syndrome, Glycogen Storage Disease I, hemangioma, hemochromatosis, hepatitis A-G, porphyria, primary biliary cirrhosis, sclerosing cholangitis, tyrosinemia, acquired liver disorders due to viral infections and/or Wilson's Disease.

Epithelial cells derived from endodermal progenitor cells of the invention can be used in cell replacement therapy to treat or alleviate symptoms of several organ diseases. The cells can be used to treat or alleviate congenital liver disorders, for example, storage disorders such as mucopolysaccharidosis, leukodystrophies, GM2 gangliosidosis; increased bilirubin disorders, for instance Crigler-Najjar syndrome; ammonia disorders such as inborn errors of the urea-cycle, for instance ornithine decarboxylase deficiency, citrullinemia, and argininosuccinic aciduria; inborn errors of amino acids and organic acids such as phenylketoinuria, hereditary tyrosinemia, α1-antitrypsin deficiency; and/or coagulation disorders such as factor VIII and IX deficiency.

Epithelial cells derived from endodermal progenitor cells of the invention can also be used in cell replacement therapy to treat or alleviate symptoms of biliary disorders such as biliary cirrhosis and biliary atresia, as well as to treat or alleviate symptoms of pancreas disorders. Further, pancreas epithelium can be made from the cells of the present invention, as well as β-cells. These cells can be used for the therapy of diabetes (subcutaneous implantation or intra-pancreas, intra-liver or kidney sub-capsular implantation). Further, the epithelial cells derived from endodermal progenitor cells of the present invention can also be used in cell replacement therapy and/or gene therapy to treat or alleviate symptoms of gut epithelium disorders such as gut atresia, inflammatory bowel disorders, bowel infarcts, and bowel resection.

Exogenous factors (e.g., cytokines, differentiation factors and other factors) can be administered prior to, after or concomitantly with the endodermal progenitor cells of the invention. For example, a form of concomitant administration would comprise combining a factor of interest in the culture media and/or pharmaceutically acceptable carrier prior to administration. Doses for administrations are variable, may include an initial administration followed by subsequent administrations; but nonetheless, can be ascertained by the skilled artisan, from this disclosure, the documents cited herein, and the knowledge in the art.

Endodermal progenitor cells of the invention or their progeny can be administered via localized injection, including catheter administration, systemic injection, localized injection, parenteral administration, or intrauterine injection into an embryo.

A method to potentially increase cell survival, when introducing the cells into a subject in need thereof, is to incorporate endodermal progenitor cells or their differentiated progeny of interest into a biopolymer or synthetic polymer. Depending on the subject's condition, the site of injection might prove inhospitable for cell seeding and growth because of scarring or other impediments. Examples of biopolymer include, but are not limited to, cells mixed with fibronectin, fibrin, fibrinogen, thrombin, collagen, and proteoglycans. This could be constructed with or without included cytokines, growth factors, differentiation factors or nucleic acid expression constructs. Additionally, these could be in suspension, but residence time at sites subjected to flow would be nominal. Another alternative is a three-dimensional gel with cells entrapped within the interstices of the cell biopolymer admixture. Again, differentiation factors, growth factors or cytokines could be included within the cells. These could be deployed by injection via various routes described herein.

An parameter involved in the therapeutic use of endodermal progenitor cells is the quantity of cells necessary to achieve an optimal effect. In current human studies of autologous mononuclear bone marrow cells, empirical doses ranging from 1 to $4 \times 10^7$ cells have been used with encouraging results. However, different scenarios may require optimization of the amount of cells injected into a tissue of interest. Thus, the quantity of cells to be administered will vary for the subject being treated. In one embodiment, between $10^4$ to $10^8$, more preferably $10^5$ to $10^7$, and most preferably $3 \times 10^7$ progenitorcells and optionally, 50 to 500 µg/kg per day of a cytokine can be administered to a human subject. However, the precise determination of what would be considered an effective dose may be based on factors individual to each patient, including their size, age, size tissue damage, and amount of time since the damage occurred. Therefore, dosages can be readily ascertained by those skilled in the art from this disclosure and the knowledge in the art.

Another parameter involved in the use of endodermal progenitor cells is the purity of the population. Pancreas or liver cells, for example, comprise mixed populations of cells, which can be purified to a degree sufficient to produce a desired effect. Those skilled in the art can readily determine the percentage of endodermal progenitor cells in a population using various well-known methods, such as fluorescence activated cell sorting (FACS). Preferable ranges of purity in populations comprising endodermal progenitor cells are about 1 to about 5%, about 5 to about 10%, about 10 to about 15%, about 15 to about 20%, about 20 to about 25%, about 25 to about 30%, about 30 to about 35%, about 35 to about 40%, about 40 to about 45%, about 45 to about 50%, about 50 to about 55%, about 55 to about 60%, about 60 to about 65%, about 65 to about 70%, about 70 to about 75%, about 75 to about 80%, about 80 to about 85%, about 85 to about 90%, about 90% to about 95% or about 95 to about 100%. Purity of the cells can be determined according to the cell surface marker profile within a population. Dosages can be readily adjusted by those skilled in the art (e.g., a decrease in purity may require an increase in dosage).

The skilled artisan can readily determine the amount of cells and optional additives, vehicles, and/or carrier in compositions to be administered in methods of the invention. Typically, any additives (in addition to the active cell(s) and/or cytokine(s)) are present in an amount of 0.001 to 50% (weight) solution in phosphate buffered saline, and the active ingredient is present in the order of micrograms to milligrams, such as about 0.0001 to about 5 wt %, preferably about 0.0001 to about 1 wt %, most preferably about 0.0001 to about 0.05 wt % or about 0.001 to about 20 wt %, preferably about 0.01 to about 10 wt %, and most preferably about 0.05 to about 5 wt %. Of course, for any composition to be administered to an animal or human, and for any particular method of administration, it is preferred to determine the toxicity, such as by determining the lethal dose (LD) and $LD_{50}$ in a suitable animal model e.g., rodent such as mouse; and, the dosage of the composition(s), concentration of components therein and timing of administering the composition(s), which elicit a suitable response. Such determinations do not require undue experimentation from the knowledge of the skilled artisan, this disclosure and the documents cited herein. And, the time for sequential administrations can be ascertained without undue experimentation.

When administering a therapeutic composition of the present invention, it will generally be formulated in a unit dosage injectable form (solution, suspension, emulsion). The pharmaceutical formulations suitable for injection include sterile aqueous solutions and dispersions. The carrier can be a solvent or dispersing medium containing, for example, water, saline, phosphate buffered saline, polyol (for example, glycerol, propylene glycol, liquid polyethylene glycol, and the like) and suitable mixtures thereof.

Additionally, various additives which enhance the stability, sterility, and isotonicity of the compositions, including antimicrobial preservatives, antioxidants, chelating agents, and buffers, can be added. Prevention of the action of microorganisms can be ensured by various antibacterial and antifungal agents, for example, parabens, chlorobutanol, phenol, sorbic acid, and the like. In many cases, it will be desirable to include isotonic agents, for example, sugars, sodium chloride, and the like. Prolonged absorption of the injectable pharmaceutical form can be brought about by the use of agents delaying absorption, for example, aluminum monostearate and gelatin. According to the present invention, however, any vehicle, diluent, or additive used would have to be compatible with the cells.

Sterile injectable solutions can be prepared by incorporating the cells utilized in practicing the present invention in the required amount of the appropriate solvent with various amounts of the other ingredients, as desired. Examples of compositions comprising progenitor cells of the invention include liquid preparations for administration, including suspensions; and, preparations for intramuscular or intravenous administration (e.g., injectable administration), such as sterile suspensions or emulsions. Such compositions may be in admixture with a suitable carrier, diluent, or excipient such as sterile water, physiological saline, glucose, dextrose, or the like. The compositions can also be lyophilized. The compositions can contain auxiliary substances such as wetting or emulsifying agents, pH buffering agents, gelling or viscosity enhancing additives, preservatives, flavoring agents, colors, and the like, depending upon the route of administration and the preparation desired. Standard texts, such as "REMINGTON'S PHARMACEUTICAL SCIENCE", 17th edition, 1985, which is incorporated herein by reference, may be consulted to prepare suitable preparations, without undue experimentation.

Compositions of the invention are conveniently provided as liquid preparations, e.g., isotonic aqueous solutions, suspensions, emulsions or viscous compositions, which may be buffered to a selected pH. Liquid preparations are normally easier to prepare than gels, other viscous compositions, and solid compositions. Additionally, liquid compositions are somewhat more convenient to administer, especially by injection. Viscous compositions, on the other hand, can be formulated within the appropriate viscosity range to provide longer contact periods with specific tissues.

The choice of suitable carriers and other additives will depend on the exact route of administration and the nature of the particular dosage form, e.g., liquid dosage form (e.g., whether the composition is to be formulated into a solution, a suspension, gel or another liquid form, such as a time release form or liquid-filled form).

Solutions, suspensions and gels normally contain a major amount of water (e.g., purified, sterilized water) in addition to the cells. Minor amounts of other ingredients such as pH adjusters (e.g., a base such as NaOH), emulsifiers or dispersing agents, buffering agents, preservatives, wetting agents and jelling agents (e.g., methylcellulose), may also be present. The compositions can be isotonic, i.e., they can have the same osmotic pressure as blood and lacrimal fluid.

The desired isotonicity of the compositions of this invention may be accomplished using sodium chloride, or other pharmaceutically acceptable agents such as dextrose, boric acid, sodium tartrate, propylene glycol or other inorganic or organic solutes.

Viscosity of the compositions, if desired, can be maintained at the selected level using a pharmaceutically acceptable thickening agent. Methylcellulose is readily and economically available and is easy to work with. Other suitable thickening agents include, for example, xanthan gum, carboxymethyl cellulose, hydroxypropyl cellulose, carbomer, and the like. The concentration of the thickener will depend upon the agent selected. The point is to use an amount, which will achieve the selected viscosity. Viscous compositions are normally prepared from solutions by the addition of such thickening agents.

A pharmaceutically acceptable preservative or cell stabilizer can be employed to increase the life of the compositions. If preservatives are used, it is well within the purview of the skilled artisan to select compositions that will not affect the viability or efficacy of the endodermal progenitor cells as described herein.

Those skilled in the art will recognize that the components of the compositions should be selected to be chemically inert. This will present no problem to those skilled in chemical and pharmaceutical principles, or problems can be readily avoided by reference to standard texts or by simple experiments (not involving undue experimentation), from this disclosure and the documents cited herein.

Compositions can be administered in dosages and by techniques well known to those skilled in the medical and veterinary arts taking into consideration such factors as the age, sex, weight, and condition of the particular patient, and the composition form used for administration (e.g., solid vs. liquid). Dosages for humans or other mammals can be determined without undue experimentation by the skilled artisan, from this disclosure, the documents cited herein, and the knowledge in the art.

Suitable regimes for initial administration and further doses or for sequential administrations also are variable and may include an initial administration followed by subsequent administrations; but nonetheless, can be ascertained by the skilled artisan, from this disclosure, the documents cited herein, and the knowledge in the art.

Endodermal progenitor cells described herein or their differentiated progeny can be genetically modified by introducing heterologous DNA or RNA into the cell by a variety of recombinant methods known to those of skill in the art. These methods are generally grouped into four major categories: (1) viral transfer, including the use of DNA or RNA viral vectors, such as retroviruses, including lentiviruses (Mochizuki, H., et al., 1998; Martin, F., et al. 1999; Robbins, et al. 1997; Salmons, B. and Gunzburg, W. H., 1993; Sutton, R., et al., 1998; Kafri, T., et al., 1999; Dull, T., et al., 1998), Simian virus 40 (SV40), adenovirus (see, for example, Davidson, B. L., et al., 1993; Wagner, E., et al., 1992; Wold, W., *Adenovirus Methods and Protocols,* Humana Methods in Molecular Medicine (1998), Blackwell Science, Ltd.; Molin, M., et al., 1998; Douglas, J., et al., 1999; Hofmann, C., et al., 1999; Schwarzenberger, P., et al., 1997), alpha virus, including Sindbis virus (U.S. Pat. No. 5,843,723; Xiong, C., et al., 1989; Bredenbeek, P. J., et al., 1993; Frolov, I., et al., 1996), herpes virus (Laquerre, S., et al., 1998) and bovine papillomavirus, for example; (2) chemical transfer, including calcium phosphate transfection and DEAE dextran transfection methods; (3) membrane fusion transfer, using DNA-loaded membranous vesicles such as liposomes (Loeffler, J. and Behr, J., 1993), red blood cell ghosts and protoplasts, for example; and (4) physical transfer techniques, such as microinjection, microprojectile J. Wolff in "Gene Therapeutics" (1994) at page 195. (see J. Wolff in "Gene Therapeutics" (1994) at page 195; Johnston, S. A., et al., 1993; Williams, R. S., et al., 1991; Yang, N. S., et al., 1990), electroporation, nucleofection or direct "naked" DNA transfer.

Cells can be genetically altered by insertion of pre-selected isolated DNA, by substitution of a segment of the cellular genome with pre-selected isolated DNA, or by deletion of or inactivation of at least a portion of the cellular genome of the cell. Deletion or inactivation of at least a portion of the cellular genome can be accomplished by a variety of means, including but not limited to genetic recombination, by antisense technology (which can include the use of peptide nucleic acids or PNAs), or by ribozyme technology, for example. Insertion of one or more pre-selected DNA sequences can be accomplished by homologous recombination or by viral integration into the host cell genome. Methods of non-homologous recombination are also known, for example, as described in U.S. Pat. Nos. 6,623,958, 6,602,686, 6,541,221, 6,524,824, 6,524,818, 6,410,266, 6,361,972, the contents of which are specifically incorporated by reference for their entire disclosure.

The desired gene sequence can also be incorporated into the cell, particularly into its nucleus, using a plasmid expression vector and a nuclear localization sequence. Methods for directing polynucleotides to the nucleus have been described in the art. For example, signal peptides can be attached to plasmid DNA, as described by Sebestyen, et al. (1998), to direct the DNA to the nucleus for more efficient expression.

The genetic material can be introduced using promoters that will allow for the gene of interest to be positively or negatively induced using certain chemicals/drugs, to be eliminated following administration of a given drug/chemical, or can be tagged to allow induction by chemicals (including but not limited to the tamoxifen responsive mutated estrogen receptor) in specific cell compartments (including, but not limited to, the cell membrane).

Any of the transfection or transduction techniques can also be applied to introduce a transcriptional regulatory sequence into endodermal progenitor cells or progeny to activate a desired endogenous gene. This can be done by both homologous (e.g., U.S. Pat. No. 5,641,670) or non-homologous (e.g., U.S. Pat. No. 6,602,686) recombination (these patents are incorporated by reference).

Successful transfection or transduction of target cells can be demonstrated using genetic markers. The green fluorescent protein of *Aequorea victoria,* for example, has been shown to be an effective marker for identifying and tracking genetically modified hematopoietic cells (Persons, D., et al., 1998). Alternative selectable markers include the β-Gal gene, the truncated nerve growth factor receptor, and drug selectable markers (including but not limited to NEO, MTX, hygromycin).

Endodermal progenitor cells of the invention can be used for many diverse clinical and pre-clinical applications, which can include, but are not limited to, use in toxicological or genomic screening methods, determination of levels of enzymes and coagulation factors, as well as treatment of the diseases disclosed herein. Endodermal progenitor cells of the invention can provide a variety of differentiated cultured cell types for high-throughput toxicological or genomic screening. The cells can be cultured in, for example, 96-well or other multi-well culture plates to provide a system for high-throughput screening of, for example, target cytokines, chemokines, growth factors, or pharmaceutical compositions in pharmacogenomics or pharmacogenetics.

Thus, the present invention provides for use of endodermal progenitor cells to detect cellular responses (e.g., toxicity) to bioactive (biologic or pharmacologic) agents, comprising contacting a culture of cells, or the differentiated progeny thereof, with one or more biologic or pharmacologic agents, identifying one or more cellular response to the one or more biologic or pharmacologic agents, and comparing the cellular responses of the cell cultures to the cellular responses of control cultures.

The invention also envisions a tissue-engineered organ, or portion, or specific section thereof, a tissue engineered device comprising a tissue of interest and optionally, cytokines, growth factors, or differentiation factors that induce differentiation into a desired cell type, wherein the endodermal progenitor cells are used to generate tissues including, but not limited to, pancreas, lung, liver, intestine, thyroid, endocrine, esophagus, colon, stomach, and gall bladder. Tissue-engineered organs can be used with a biocompatible scaffold to support cell growth in a three-dimensional configuration, which can be biodegradable. Tissue-engineered organs generated from the endodermal progenitor cells can be implanted into a subject in need of a replacement organ, portion, or specific section thereof. The present invention also envisions the use of the endodermal progenitor cells or cells differentiated therefrom as part of a bioreactor, e.g., a liver assist device.

Homogenous organs, portions, or sections derived from the endodermal progenitor cells of the invention can be implanted into a host. Likewise, heterogeneous organs, portions, or sections derived from endodermal progenitor cells induced to differentiate into multiple tissue types can be implanted into a subject in need thereof. The transplantation can be autologous, such that the donor of the stem cells from which organ or organ units are derived is the recipient of the engineered tissue. The transplantation can be heterologous, such that the donor of the stem cells from which organ or organ units are derived is not that of the recipient of the engineered-tissue (e.g., allogeneic or xenogenic).

Once transferred into a host, the tissue-engineered organs can recapitulate the function and architecture of the native host tissue. The tissue-engineered organs will benefit subjects in a wide variety of applications, including the treatment of cancer and other diseases disclosed herein, congenital defects, or damage due to surgical resection.

EXAMPLE

The following example is provided in order to demonstrate and further illustrate certain embodiments and aspects of the present invention and is not to be construed as limiting the scope thereof.

Expansion and Characterization of Pancreas-Derived Endodermal Progenitor Cells (PDPCs)

Materials and Methods

Transgenic Animals. For mouse experiments the following transgenic strains were used: Pdx1 -GFP (Gioquiang Gu, Vanderbilt University, Nashville, Tenn.), MIP-GFP (Manami Hara, University of Chicago, Chicago, Ill.), Actb-GFP (Makio Ogawa, Medical University of South Carolina, Charleston, S.C.), Ins2cre (Jackson Labs, Bar Harbor, Me.), Pdx1cre (Pedro Herrera, University of Geneva), Actbcre (Jackson Labs), Z/EG (Jackson Labs), and Rag2γc$^{-/-}$ (Taconic Labs, Hudson, N.Y.) (Cao et al. 1995). While Actb-GFP and Rag2γc$^{-/-}$ breeders were maintained as homozygotes, all other breeders were maintained as heterozygotes and transgenic offspring were genotyped by PCR using Platinum Taq DNA Polymerase (Invitrogen, Carlsbad, Calif.) as per manufacturers conditions using the following cycling protocol: 1) 95° C.-2 min, 2) 95° C. -30sec, 59° C.-30sec, 72° C.-30sec (35 cycles), 3) 72° C.10 min. PCR products were visualized on a 2% agarose gel. Primers used included the following:

```
GAPDH,
F: CATGGCCTTCCGTGTTCCTA,        (SEQ ID NO: 1)

R: CTGGTCCTCAGTGTAGCCCAA;       (SEQ ID NO: 2;
                                151 bp)

Pdx1-GFP,
F: ATGAGCAAGGGCGAGGAACTGTTC,    (SEQ ID NO: 3)

R: GTGTCACCTTCGAACTTGACTTC;     (SEQ ID NO: 4;
                                353 bp)

Z/EG,
F: ACTATCCCGACCGCCTTACT,        (SEQ ID NO: 5)

R: CTGTAGCGGCTGATGTTGAA;        (SEQ ID NO: 6;
                                175 bp)

Ins2cre,
F: CTCTGGCCATCTGCTGATCC,        (SEQ ID NO: 7)

R: CGCCGCATAACCAGTGAAAC;        (SEQ ID NO: 8;
                                550 bp)

Pdx1cre,
F: ACTACATCTTGAGTTGCAGGC,       (SEQ ID NO: 9)

R: CCTGTTTTGCACGTTCACCG;        (SEQ ID NO: 10;
                                700 bp)

Actbcre,
F: CTTCAGGCGCGCGGTCTGG,         (SEQ ID NO: 11)

R: GAGACGGAAATCCATCGCTC.        (SEQ ID NO: 12;
                                452 bp)
```

For Cre recombinase-mediated lineage tracing, Ins2cre and Pdx1cre and Z/EG offspring were bred and resultant double transgenic offspring were used in subsequent studies. All transgenic animals were bred and maintained under SPF conditions in partial autoclave cages. University of Minnesota Research Animal Resources housing and husbandry guidelines are adapted from requirements in the Animal Welfare Act and *The Guide for the Care and Use of Laboratory Animals* (National Academy Press, 1996) (Grossblatt 1996).

Isolation and Culture of Mouse Pancreatic Fractions.

1. Islet-Enriched Fraction: Adult mice (10-24 weeks) were anesthetized by an IP dose of Avertin (250 mg/kg), after which the abdomen was opened. The pancreas was perfused with 2.5 mL Liberase RI (Roche, Indianapolis, Ind.) in HBSS (Mediatech, Hemdon, Va.)+0.1 mg/mL DNase I (Roche), 25 mM HEPES (Mediatech) and digested at 37° C. for 14 min. Digested pancreata were washed 3× in HBSS+10% FBS (Hy-Clone, Logan, Utah) and islets were purified using a continuous density gradient as described previously (Guo et al. 2003). Islet-enriched preparations were 30-60% pure as determined by staining with Dithizone (Sigma, St. Louis, Mo.). The islet enriched fraction was cultured overnight in culture medium (CM) consisting of 60:40 low-glucose DMEM (Mediatech):MCDB201 (Sigma)+2% FBS, 10 ng/ml human EGF (Sigma), 10,000 U/mL Lif (Chemicon, Temecula, Calif.), 10,000 I.U. Penicillin/mL, 10,000 µg/mL Streptomycin (Mediatech), $10^{-4}$ M ascorbic acid 2-phosphate (Sigma), 25 mM HEPES (Mediatech), 0.1 mM 2-Mercaptoethanol (Invitrogen), 1 mg/ml BSA (Sigma) in 60 mm hydrophobic dishes (Sarstedt, Newton, N.C.) at 37° C. and 5% $CO_2$. For PDPC expansion, islet-enriched fractions were seeded at 10-20 islets/cm$^2$ in tissue cultured treated dishes (BD Biosciences, San Jose, Calif.) coated with 10 µg/mL fibronectin (Sigma). Complete media changes were done every 2-3 days for 1 week, after which media was not changed further.

2. Unfractionated Pancreas: Adult mice (10-24 weeks) were anesthetized and pancreata perfused as described above for isolation of the islet-enriched fraction. Digested pancreata were cultured for two days in CM in hydrophobic flasks (Sarstedt). To improve cell viability, suspension cultures were washed after 24 hrs with PBS+1 mg/ml BSA. For PDPC expansion, unfractionated pancreas was seeded at a cell pellet dilution of 1:750 v/v in CM. Complete media changes were made every 2-3 days for 1 week as done for islet-enriched cultures. Successful generation of PDPCs from islet-enriched or total pancreas fraction was >75%.

3. Differentiation of PDPCs: CD45⁺ cells from 12-14 day islet-enriched fraction cultures were seeded at 7-10×10⁴ cells/cm² on Type 1 collagen (10 μg/cm²)(Upstate, Charlottesville, Va.) coated 48 well-plates (BD Biosciences). Cells were seeded in CM supplemented with 10% FBS+20 ng/ml HGF (Sigma), 100 nM Dexamethasone (sigma), and 0.25× ITS (Sigma). Media changes were made every 7-14 days. Cells were analyzed after 3-6 weeks.

RNA Isolation, cDNA Synthesis and Quantitative Real-Time PCR.

Total RNA ($1\times10^5$-$1\times10^6$ cells) was isolated using an RNeasy Micro Kit (Qiagen, Valencia, Calif.). Eluted RNA was treated with Turbo DNA-free according to the manufacturers protocol (Ambion, Austin, Tex.) and reverse-transcribed into cDNA using Superscript III with random hexamers (Invitrogen). As relative expression controls, mouse liver total RNA (Ambion), mouse pancreas mRNA (Clontech, Mountain View, Calif.), mouse liver F2 oval cell-containing fraction (X. Wang, University of Minnesota) or mouse total bone marrow was reverse transcribed similarly and used in real-time qPCR analysis. For real-time qPCR, 5-10 ng cDNA was amplified using SYBR® Green PCR Master mix with an ABI Prism 7700 (Applied Biosystems, Foster City, Calif.) under the following conditions: 1) 50° C.-2 min 2) 95° C.-10 min 3) 95° C. -15 sec, 59° C.-60 sec (40 cycles), 4) 95° C.-15 sec, 59° C.-20 sec, 95° C.-15 sec (Dissociation Curve Analysis). In addition to dissociation curve analysis, PCR products were verified by gel electrophoresis. Primer used for real-time qPCR are listed provided in FIG. 1.

FACS Analysis. To analyze PDPCs and select sub-populations from PDPC cultures, cells were harvested after 14-21 days using 0.25% trypsin (Mediatech), washed with PBS+2% FBS (HyClone), 1mM EDTA (Ambion) (F2-PBS), and filtered through a 40 μm cell strainer (BD Bioscience). For FACS analysis, $1\times10^5$ cells were stained with anti-mouse CD45-APC (30-F11), CD45-PE (30-F11), CD45-PE-Cy7 (30-F11), Sca1-PE (E13-161.7), CD34-PE (RAM34), Thy1-PE (30-H12), Mac1-PE (M1/70) (BD Bioscience), or CD115-PE (eBioscience, San Diego, Calif.) antibodies and analyzed using a FACSCalibur flow cytometer (BD Bioscience).

Selection of Subpopulations from PDPC Cultures. To isolate sub-populations from PDPC cultures, cells were stained with CD45-APC, CD45-PE, or Sca1-PE and selected using a FACSAria flow cytometer (BD Biosciences). Alternatively, cells from PDPC cultures were labeled with anti-mouse CD45-PE, CD45-FITC (104), or CD45-Biotin (104) (BD Biosciences) and purified using the immunomagnetic EasySep™ PE selection kit (Stem Cell Technologies, Vancouver, BC). Cells were analyzed for purity by FACS prior to use in subsequent experiments.

Immunofluorescence and Immunohistochemistry. To stain PDPC cultures for CD45⁺ cells, cultures were washed 2× with F2-PBS, incubated for 15 minutes with CD45-PE (BD Bioscience), followed by 2× wash with F2-PBS. To stain PDPC cultures for smooth muscle actin, PDPC cultures were fixed (15 min) with 4% formalin, incubated (15 min) with 100 mM glycine (Sigma) in PBS, washed 3× PBS, incubated (15 min) with 0.1% Tween-20 (Sigma) in PBS, washed 3× PBS, blocked (30 min) in 0.4% fish skin gelatin (Sigma) and stained overnight (4° C.) with monoclonal mouse anti-smooth muscle actin (Sigma) (1A4). Following overnight incubation, cells were stained (45 min-room temperature) with anti-mouse AlexaFluor 594 (Invitrogen) and washed 4× (15 min) in 0.1% Tween in PBS. For immunohistochemistry on differentiated samples, cells were fixed with 4% formalin (12 min) and staining was performed using the streptavidin-biotin-peroxidase method as per the manufacturer's protocol (Dako, Glostrup, Denmark) with goat anti-Hnf-3β(P-19)(sc-9187) (Santa Cruz Biotechnology, Inc, Santa Cruz, Calif.). As a positive staining control, the Hepa1-6 hepatoma cell line (ATCC, Manassas, Va.) was used. These cells were maintained in high-glucose DMEM (Mediatech) supplemented with 10% FBS (Hyclone). Hepa1-6 cells were fixed and stained using the same protocol applied to differentiation cultures.

Hematopoietic Chimeras. Bone marrow was harvested from 6-8 week old Actb-GFP mice, red blood cells lysed with ammonium chloride (Stem Cell Technologies, Vancouver, BC), and in some instances cells were labeled with anti-mouse CD117(c-Kit)-APC (2B8), Sca1-PE (E13-161.7), hematopoietic lineage cocktail-biotin (Gr-1 (RB6-8C5), CD11b (M1/70), CD4 (GK1.5), CD8a (53-6.7), Ter-119 (Ly-76), and CD45R/B220 (RA3-6B2) followed by staining with streptavidin-PerCp (BD Bioscience). GFP⁺ KSL (c-Kit⁺/Sca-1⁺lineage market⁻; Ikuta and Weissman 1992) cells were sorted on the FACSAria. Rag2γc⁻/⁻ immunodeficient recipient mice were sub-lethally irradiated with 750cGy cesium and injected (intra-venous, tail vein) with $1\times10^6$ GFP⁺ mononuclear bone marrow cells or $1\times10^4$ GFP⁺ KSL-HSCs along with $2\times10^5$ wild-type C57B16 mononuclear bone marrow cells. Peripheral blood samples of recipient mice were taken at 2-3 months post-transplant and analyzed by flow cytometry for CD45 and GFP to determine % CD45⁺ hematopoietic engraftment. Positively engrafted mice were used for subsequent experiments.

To generate chimeric Cre-Z/EG mice, recipient Z/EG reporter mice were lethally irradiated with 950 cGy cesium and injected (intra-venous, tail vein) with $1\times10^6$ Actbcre mononuclear bone marrow cells. To determine engraftment, peripheral blood samples from recipient mice were analyzed after 2 months post-transplant and analyzed by PCR using Platinum Taq DNA Polymerase (conditions as described above) using the following primer set:

```
Cre,
F: CGTACTGACGGTGGGAGAAT, (SEQ ID NO: 13)

R: CCCGGCAAAACAGGTAGTTA. (SEQ ID NO: 14; 166 bp)
```

Molecular Evaluation of Cre Recombinase Lineage Tracing.

Genomic DNA was isolated using the QIAamp DNA micro kit (Qiagen), and Platinum Taq PCR was performed using the following excision specific PCR primer sets:

```
CAAGS-LacZ,
F: GTTCGGCTTCTGGCGTGT,    (NO: 15)

R: GTTGCACCACAGATGAAACG;  (SEQ ID NO: 16; 750 bp)

CAAGS-GFP,
F: GTTCGGCTTCTGGCGTGT,    (SEQ ID NO: 17)

R: GTAGGTCAGGGTGGTCACGA.  (SEQ ID NO: 18; 500 bp)
```

Excision PCR reaction condition were : 1) 95° C.-2 min, 2) 95° C.-30 sec, 59° C.-30 sec, 72° C. -60 sec (40 cycles), 3) 72° C.-10 min. PCR products were visualized on a 2.0% agarose gel.

Results

Generation of Pancreas-Derived Endodermal Progenitor Cells (PDPCs) from Pancreas. Mouse islet-enriched pancreas fraction or unfractionated pancreas were cultured in suspension conditions for 2 days in low serum containing medium supplemented with EGF and LIF to induce spheroid (cluster) formation (FIG. 2). Resultant clusters were seeded in the same media onto fibronectin coated dishes and quickly adhered, spread, and formed colonies of epithelial cells among cells with mesenchymal morphology. To facilitate the expansion of the mesenchymal-like cells, the culture medium was changed every 2-3 days. After 1 week, the medium was no longer changed which limited mesenchymal-like cell proliferation and supported the rapid appearance and proliferation of a distinct round or oval-shaped cell population surrounding islet clusters. This emerging population was termed pancreas-derived endodermal progenitor cells or PDPCs. PDPCs could be generated from either the unfractionated or the islet-enriched fractions, but isolation from unfractionated pancreas yielded more PDPCs/mouse pancreas ($1\text{-}3\times10^5$). Moreover, resultant PDPCs were phenotypically indistinguishable (data not shown).

Figure 3A:
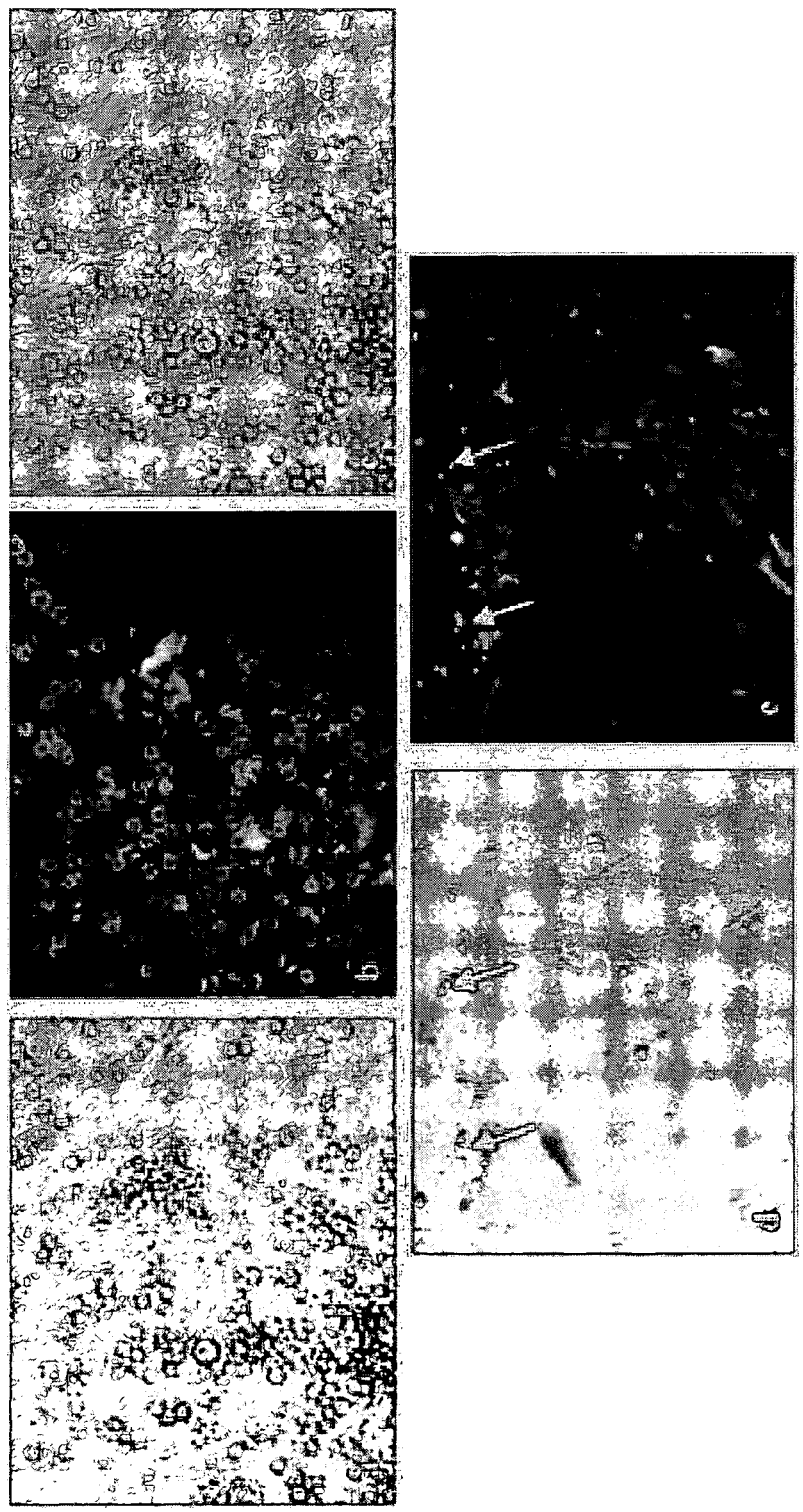
FIG. 3 depicts the characterization of PDPCs by immunohistochemistry, FACS and real-time qRT-PCR which reveal coexpression of hematopoietic, endodermal and endothelial markers. (A) Day 14, PDPC cultures initiated with MIP-GFP pancreata were stained on day 14 with anti-CD45 (Alexa 594, yellow, panel b). $CD45^+$ cells are GFP negative (panel b and panel c=merge a+b). The mesenchymal cells stained positive with anti-smooth muscle actin (Alexa 594, red, panel e). Cells were counterstained with DAPI. White arrows (panel d and e) show small round PDPCs growing on top of the smooth muscle actin$^+$ mesenchymal cells. Figures a-e=20×. Stainings are representative of 2 independent experiments. (B) Cells were harvested from PDPC cultures on d12-14 and labeled with anti-CD45, Sca1, CD34, Thy1, Mac1 and CD115 antibodies. Data shown is representative of 2 independent experiments. (C and D) Real-time qRT-PCR results on immunomagnetic purified $CD45^+$ cells (pooled RNA from three independent isolations; purity 95.2±0.84%) (C) or FACS purified $CD45^+Sca1^+/CD45^+Sca1^-$ cells (D) from day 12-14 PDPC cultures. Shown is relative expression compared to a primary F2 hepatic oval cell-containing fraction. $\Delta Ct=Ct$ (Gene-of-Interest)$-Ct$ (Reference Gene). Expression Levels: $++++=\Delta Ct=<6$, $+++=\Delta Ct=6-12$, $++=\Delta Ct=12-18$, $+=\Delta Ct=>18$. ND=Not Detected, NT=Not Tested.
Figure 3B:
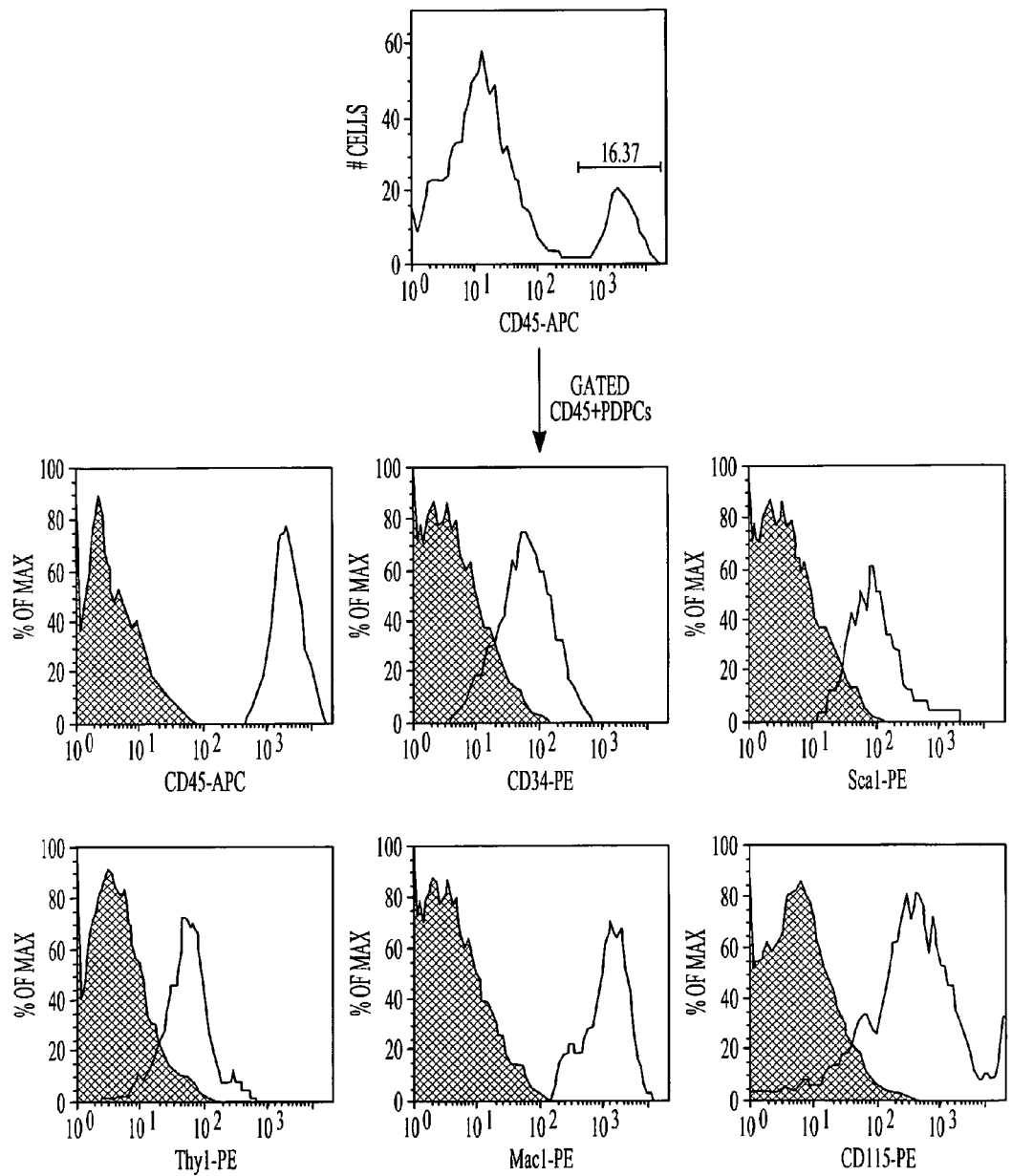

When cultures were initiated with pancreata from Pdx1-GFP (Gu et al. 2004) transgenic animals in which beta-cells are GFP positive, dense colonies of PDPCs began to emerge on top of the layer of mesenchymal cells, with the most abundant growth observed near adherent GFP$^+$ islet clusters (FIG. 2). However, few, if any, PDPCs were GFP-positive. Immunofluorescence staining on late-stage PDPC cultures revealed that the round cell population was positive for the pan-leukocyte marker CD45, while the adherent mesenchymal cells were positive for smooth muscle actin (FIG. 3A). Flow cytometry confirmed that PDPCs were positive for CD45 as well as the hematopoietic stem/progenitor cell markers CD34, Sca1, Thy1 and the monocyte markers Mac1 and CD115 (FIG. 3B). PDPCs were, however, negative for the granulocyte, B-cell, and T-cell lineage markers Grl, B220, CD4 and CD8, respectively (data not shown).

Figures 3D, 4A:
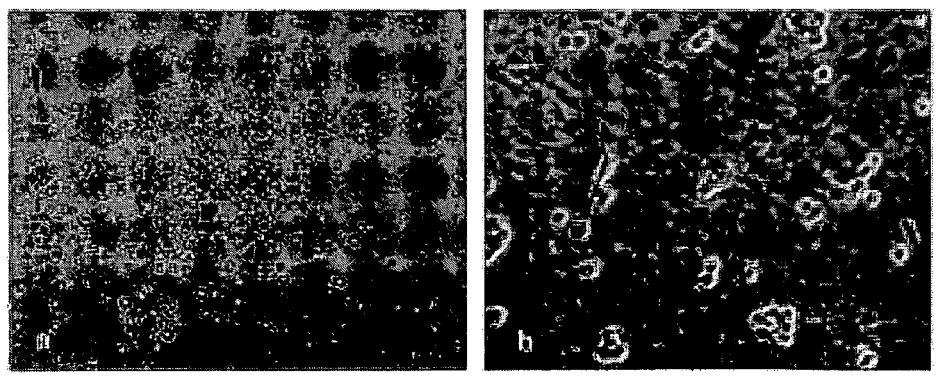
FIG. 4 depicts PDPCs differentiated for 4-6 weeks with high serum, HGF, and dexamethasone. (A) Light microscopy of $CD45^+$ PDPCs (94-98% pure) cultured for 4-6 weeks on type I collagen in medium containing 10% FCS, 20 ng/mL HGF and dexamethasone. (B) Real-time qRT-PCR of cells at the time of seeding (d0) and on cells harvested after 4-6 weeks in differentiation conditions. Results are expressed relative to mouse total liver except *=relative to mouse total pancreas. Differentiation data represents average results of two independent differentiations. $\Delta Ct=Ct$ (Gene-of-Interest)$-Ct$ (Reference Gene). Expression Levels: $++++=\Delta Ct=<6$, $+++=\Delta Ct=6-12$, $++=\Delta Ct=12-18$, $+=\Delta Ct=>18$. ***=Marker analyzed on only n−1 differentiation. (C) Immunohistochemistry of PDPCs cultured under differentiation conditions for 3-4 weeks. Control (d, e, f) is the Hepa1-6 hepatoma cell line. (a and d) isotype control, (b and e) Hnf3β-DAB (20×), (c and f) Hnf3β-DAB (40×).

Quantitative real-time PCR on CD45$^+$ enriched PDPCs revealed expression of additional hematopoietic stem/progenitor markers including Lmo2, Runx1, HoxB4, Scl (Tal1), Gata2, Ikaros, Kit, Blnk, PU.1, and Cxcr4 (not hematopoietic specific) (FIG. 3C). Enriched CD45$^+$ PDPCs also expressed significant levels of early endoderm/epithelial markers (Afp, Met, Ttr, Sox7, CKs 7, 8, 18, 19 and Cdh1) and endothelial markers (Flk1, Cdh5, CD31, and vWF) (FIG. 3C, FIG. 4B). Since many of these markers are also expressed by hepatic oval cells, expression of many of these transcripts in PDPCs were compared to a primary isolated mouse hepatic F2 oval cell-containing fraction, a size purified fraction that has been observed to arise during DDC-induced mouse liver regeneration (Wang et al. 2003). Compared to the F2 fraction, PDPCs expressed higher levels of most hematopoietic transcripts and the early endodermal transcripts Afp and Sox7, but expressed lower levels of the epithelial transcripts CK7, CK19, Cdh1 and endothelial transcripts. The CD45$^+$ Sca1$^+$ purified subpopulation expressed higher levels of CK7, CK19, and Cdh1, (60.71%, 12.59%, and 13.82%, respectively, compared to the F2 fraction) compared to only CD45$^+$ cells. (FIG. 3D). Similar to oval cells, PDPCs were also found to produce numerous cytokines and growth factors including MCSF, MIP1β, MIP1γ, MIP2, MCP1, MCP3, MCP5, IL-6 and SCF, as determined by ELISA and real-time RT-qPCR (data not shown) (Knight et al. 2005; Fujio et al. 1996).

Endoderm Differentiation of PDPCs. In late-stage cultures, PDPCs underwent morphological changes from small and round to a more flattened shape, suggesting that they might be able to differentiate to more mature epithelial/endoderm cells. Therefore, CD45$^+$ immunomagnetic purified PDPCs (94-98% pure) (FIG. 4A-a) were cultured for 4-6 weeks on Type I collagen coated plates with 10% FBS and HGF, a factor previously shown to direct stem cells to a hepatic fate (Schwartz et al. 2002; Schwartz et al. 2005). During the first 7-10 days after plating, PDPCs adhered, spread, and began to proliferate. After 1-2 weeks in culture, proliferation ceased and the vast majority (>80%) of the cells acquired a flattened morphology (FIG. 3A-b). Real-time RT-qPCR demonstrated a 20 to 130-fold increase in most epithelial transcripts (CK7, 8, 18, 19 and Cdh1) (FIG. 4B) (n=2). In addition, many endodermal transcription factors (Hnf1β, Hnf3α, Hnf3β, Hnf4 and Hnf6), which were initially expressed at low or undetectable levels, were up-regulated between 290 and 1,950-fold. Expression of Afp was significantly lower whereas levels of the mature hepatocyte transcripts Ttr, Albumin, Cyp2b13, and Cyp1a1 was significantly increased (FIG. 4B). Compared to mouse liver, most epithelial markers and many transcription factors (including Gsc, Sox17, Hnf1β and Hnf3β) were expressed at near equal or greater levels. Interestingly, expression of some pancreatic transcripts (Pdx1 and Nkx6.1) were also increased, but levels of Ins2 were decreased suggesting a lack of robust beta-cell differentiation. It is noteworthy that the expression level of CD45 remained relatively constant during differentiation (FIG. 4B), suggesting the results are not likely caused by the outgrowth of a small contaminating CD45$^-$ sub-population.

Figure 4C:
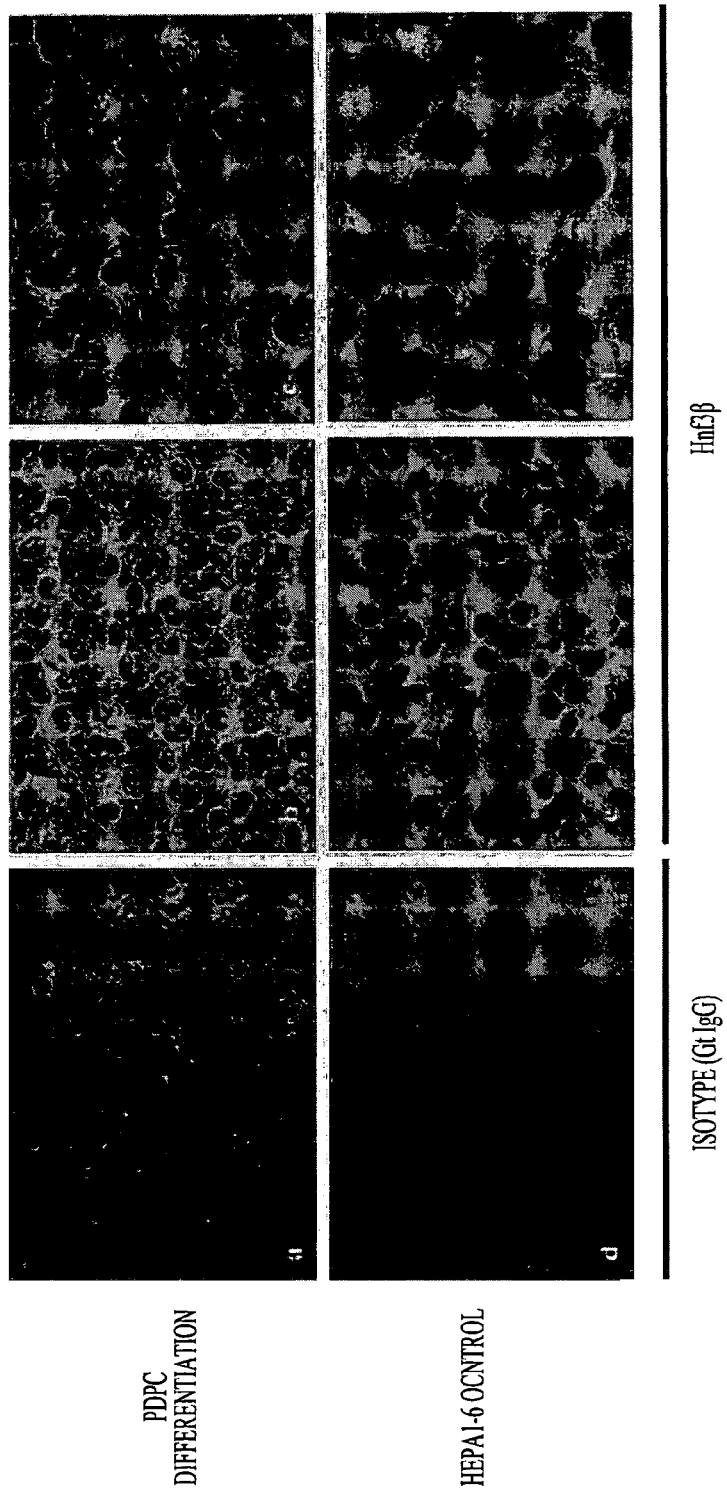

The upregulation seen by real-time qPCR for Hnf3β (FIG. 4C) was confirmed by immunohistochemistry on cells allowed to differentiate for 3-4 weeks (n=2). Staining results displayed areas of cultures with distinct nuclear staining for Hnf3β (FIG. 4-b, c), in a manner similar to that seen for control Hepa1-6 cells (FIG. 4C-e, f). Positively stained cells displayed a flattened epithelioid morphology, with some visible binucleated cells (FIG. 3C-b, c).

Figure 5A:
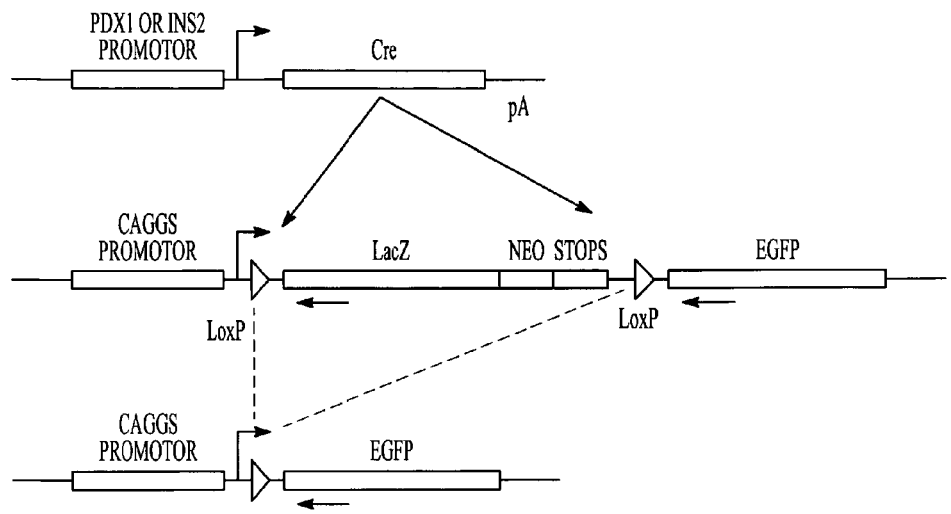
FIGS. 5A-D. PDPCs are not of an endodermal pancreatic origin. (A) PCR-based detection of lineage tracing employs a common forward CAAGS primer (black arrows) and specific reverse primers (blue, LacZ; green, GFP), allowing detection of Z/EG reporter excision events. (B) Pancreata from Ins2-Cre×Z/EG (ZI) double transgenic animals constitutively express GFP in mature beta-cells (a) and pancreata from Pdx1 cre×Z/EG (ZPC) double transgenic animals display GFP labeling in all pancreatic cell types (c). Under PDPC culture conditions for 14 days, neither ZI (b) nor ZPC (d) derived PDPCs were GFP positive. (C) PDPCs harvested on d14 from cultures initiated with pancreata from ZI (a) or ZPC (b) animals, labeled with anti-CD45-PE and analyzed by FACS.
Figure 5B:
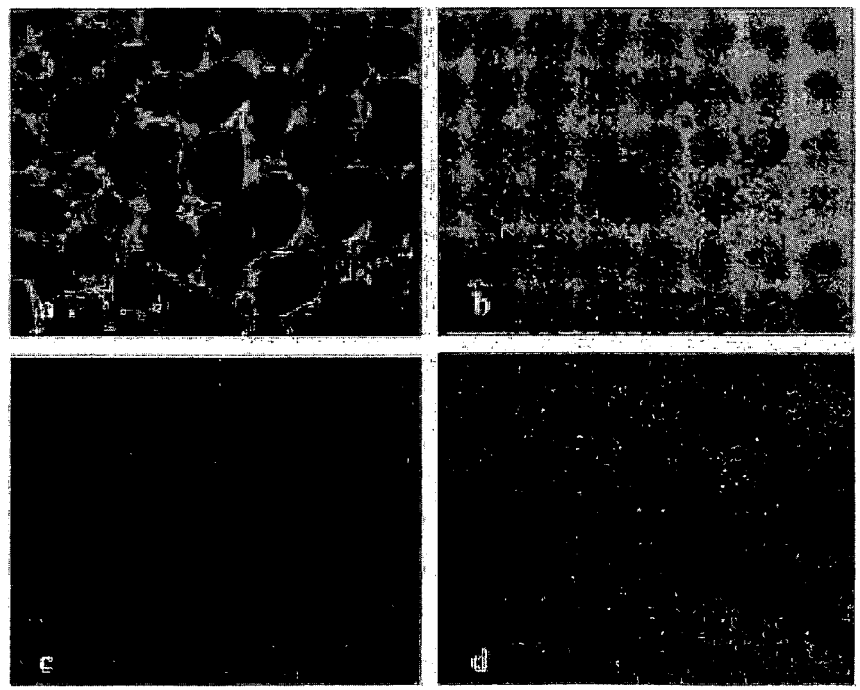
Figure 5C:
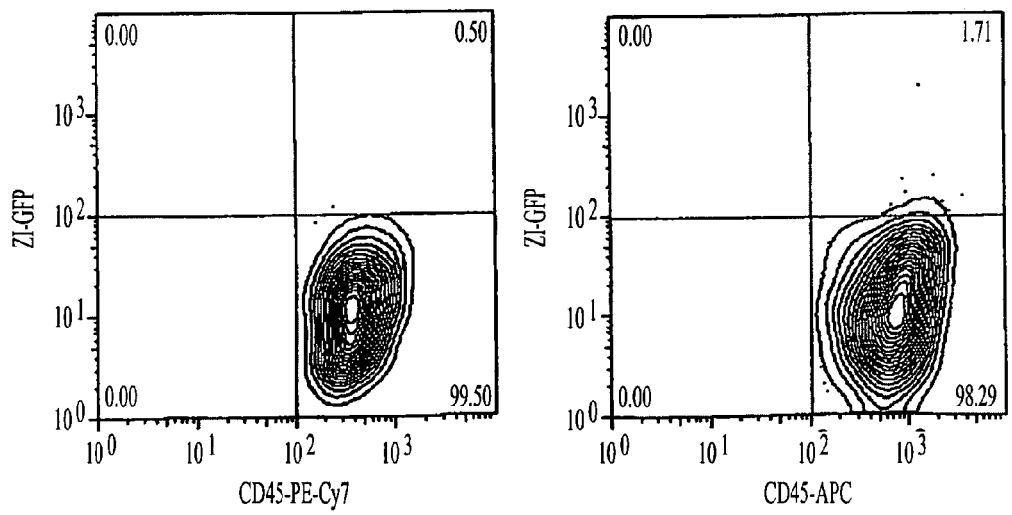
Figure 5D:
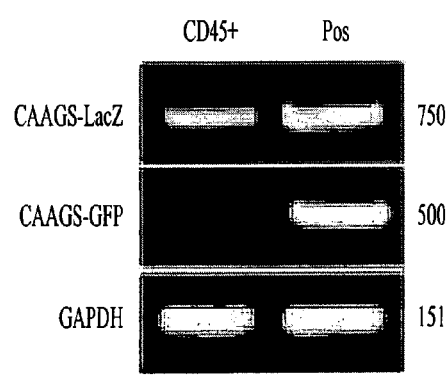

Pancreatic Lineage Tracing of PDPCs. To establish the origin of PDPCs, it was first tested whether they were derived from pancreatic endoderm or possibly mature beta-cells. To address this, Pdx1cre-Z/EG (ZPC) and Ins2cre-Z/EG (ZI) double-transgenic lineage tracing animals were generated. These mice provide Pdx-1 or Ins2 promoter-specific expression of the bacteriophage P1 Cre-recombinase in addition to the Z/EG reporter construct. In agreement with previously published data (Postic et al., 1990; Gannon et al. 2000; Novak et al. 2000), in ZI animals islet-specific GFP-expression was seen (FIG. 5B-a), while in ZPC animals all pancreatic cells were GFP positive (FIG. 5B-c). In none of the ZI or ZPC cultures established were significant levels of GFP positive PDPCs detected as evaluated by direct immunofluorescence microscopy (FIG. 5B-b,d) and FACS for CD45 and GFP (FIG. 5C-a,b). To exclude the possibility that the GFP expression was silenced, primer sets were designed which utilize a common CAAGS-specific forward primer with two unique reverse primers, one specific for GFP and the other LacZ (FIG. 5A). PCR amplification using the CAAGS-LacZ primer set amplifies a product in the unexcised Z/EG reporter construct, while the CAAGS-GFP primer set only amplifies the resultant excised construct. PCR on genomic DNA isolated from FACS-purified (>99%) CD45$^+$ ZPC PDPCs displayed amplification of only the CAAGS-LacZ PCR product (FIG. 5D, lane 1). In addition, real-time qPCR of the same sample using the CAAGS-GFP primer set revealed only 0.002% excision as compared to an Actbcre-Z/EG (100%) excision control (data not shown). This very low level of excision is likely caused by low levels (<1%) of contamination during FACS purification.

Total Bone Marrow and KSL-HSC Lineage Tracing. As PDPCs express a large number of hematopoietic markers, it was tested whether they are bone marrow (BM) derived, as has also been suggested for hepatic oval cells (Petersen et al. 1999). Sublethally irradiated Rag2γc$^{-/-}$ recipient mice were reconstituted with total BM from Actb-GFP transgenic animals. Rag2γc$^{-/-}$ mice are defective in the recombinase activating 2 gene and are therefore unable to carry out V(D)J rearrangement. These mice fail to generate mature T or B lymphocytes, but otherwise have apparently normal hematopoiesis (Cao et al.

Figure 6A:
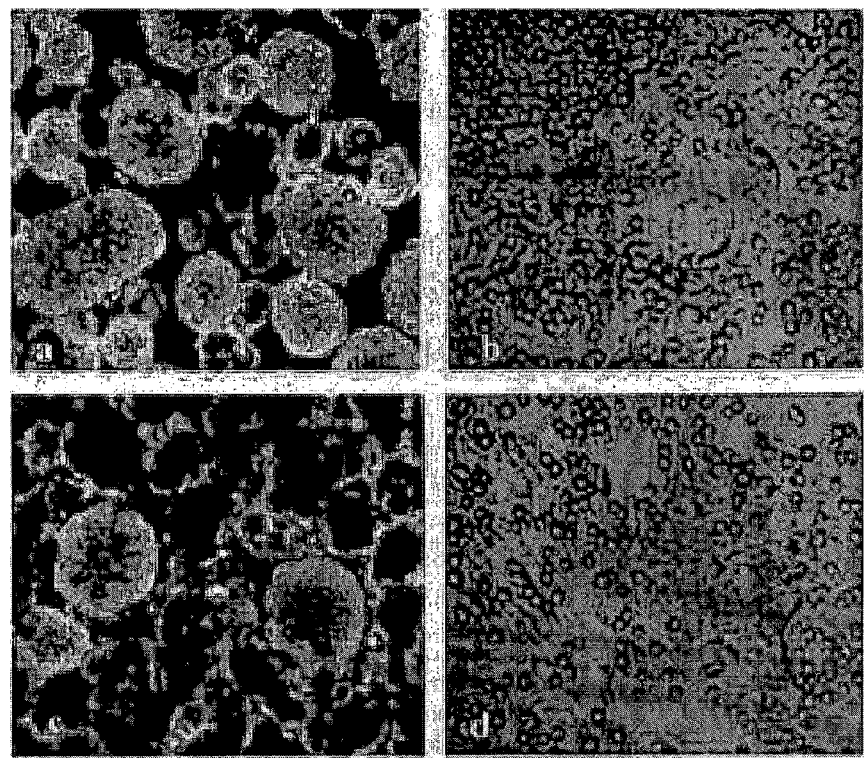
FIG. 6. PDPCs are derived from the hematopoietic stem cell enriched KSL fraction of bone marrow. (A) Total BM (a) or KSL cells (c) from Actb-GFP mice were transplanted in lethally irradiated Rag2γc$^{-/-}$ mice. Three months later, pancreata were harvested. GFP$^+$ cells could be seen predominantly in islet clusters (a, c). Pancreata were cultured under PDPC conditions and evaluated on d12-14 by immunofluorescence (b, d). The majority of PDPCs were GFP+. Representative example of 3 independent isolations each for total BM and KSL experiments. (B) PDPCs were harvested on day 14 from cultures initiated with pancreata from GFP+ BM (a) or KSL (b) grafted animals and labeled with anti-CD45-PE and analyzed by FACS.
Figure 6B:
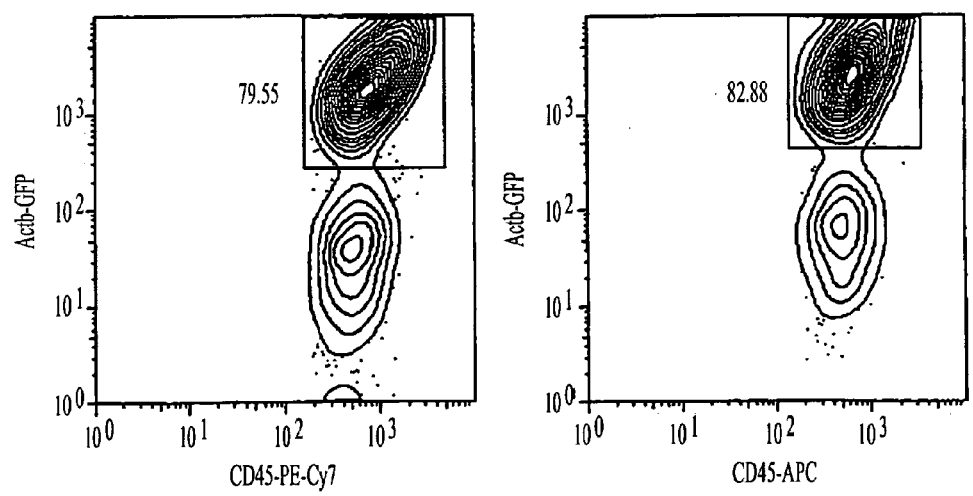

1995). Examination of the islet-enriched pancreatic fractions harvested from hematopoietic chimeras 3-months after transplantation, revealed that the vast majority of GFP$^+$ cells reside within the islet compartment (FIG. 6A-$a$). Late-stage cultures (n=3) displayed robust, uniform GFP-labeling of PDPCs (FIG. 6A-$b$), confirmed by FACS for CD45 and GFP (FIG. 6B-$a$), indicating that PDPCs are derived from cells within the BM. FACS purified GFP$^+$KSL cells, enriched for hematopoietic stem cells, were grafted into irradiated Rag2γc$^{-/-}$ recipient mice (n=3). At 2-3 months post transplant, 91.20±4.36% (% GFP$^{30}$ CD45$^+$ PDPC vs. % GFP$^+$ CD45$^+$ total BM) of PDPCs were CD45$^+$GFP$^+$ and hence derived from the GFP$^+$KSL BM-derived graft (FIG. 6B-$b$) Although PDPCs have a KSL BM origin and a hematopoietic progenitor phenotype, they did not form hematopoietic colonies in a methylcellulose colony forming assay, a commonly employed assay for the determination of hematopoietic progenitor potential (data not shown).

Figure 7A:
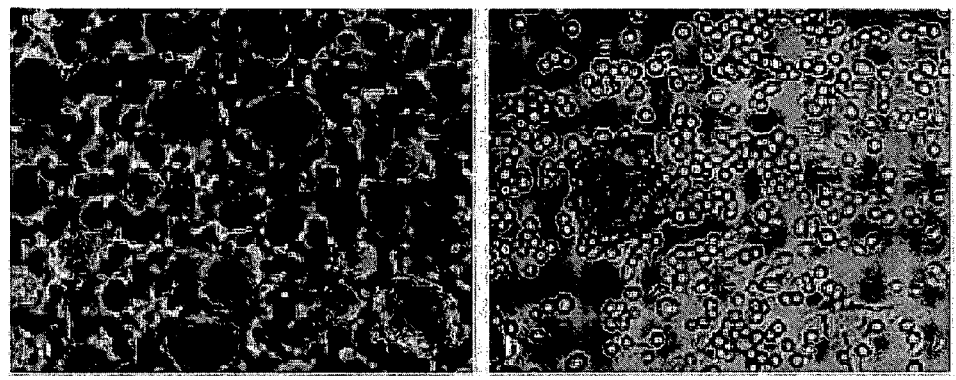
FIG. 7. PDPCs are not the result of BM-derived cells fusing with pancreas cells. (A) The islet-enriched fraction of pancreata from Z/EG animals grafted with BM from Actbcre did not show visible GFP+ cells at d0 (a). When cells were cultured for 14 days under PDPC culture conditions, PDPCs were not GFP+ (b). (B) PDPCs were harvested from cultures on day 14 and labeled with anti-CD45-PE and confirmed by FACS. (C) DNA was obtained from FACS purified CD45+ PDPCs isolated from grafted animals and PCR was performed using CAAGS-LacZ and CAAGS-GFP and Cre primers to detect excision and the presence of Actbcre-derived CD45+ PDPCs.
Figure 7B:
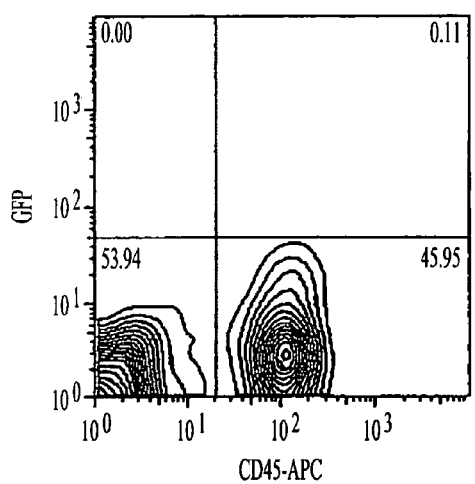
Figure 7C:
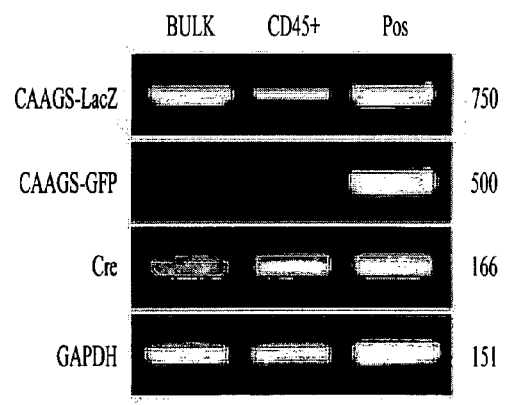

Determination Whether Fusion Between Bone Marrow Cells and Pancreas Derived Cells Underlies the Generation of PDPCs. As fusion has been recognized as a mechanism for BM plasticity both in vivo (Wang et al. 2003) and ex vivo (Terada et al. 2002), it was tested whether PDPCs are derived from BM-derived cells that fuse with pancreatic cells in vivo or ex vivo. To test this, recipient Z/EG reporter mice were lethally irradiated and injected with Actbcre total BM cells. As these cells provide ubiquitous expression of Cre-recombinase, resultant BM-derived PDPCs in this model will express Cre and will coexist with recipient Z/EG pancreatic cells. If PDPCs were derived from fusion between BM-derived cells and pancreatic cells in vivo or ex vivo, expression of the Cre and Z/EG genes in the same cell should result in excision of the LoxP-flanked cassette and will result in GFP-fluorescence (Doyonnas et al. 2004). Primary islet-enriched fractions and late-stage PDPC cultures from these animals showed no detectable GFP-fluorescence in unpurified (bulk) and CD45$^+$ enriched PDPCs (FIGS. 7A and B). Excision PCR was performed and displayed no evidence of excision in bulk and CD45$^+$ fractions (FIG. 7C). It is noteworthy that significant levels of Cre genomic DNA was detected by PCR in the CD45$^+$ fraction, ensuring a significant presence of Cre donor-derived PDPCs (FIG. 7C, lane 2). Real-time qPCR for the CAAGS-GFP primer set revealed 0.23% excision in the CD45$^+$ fraction and 1.96% excision for the bulk culture (data not shown), supporting an overall lack of fusion in the PDPC culture system.

BM-Derived Sca1$^+$ Cells Cocultured with Pancreas In Vitro Do Not Acquire a PDPC Phenotype. To determine whether BM cells acquire a PDPC phenotype because of coculture with pancreatic cells ex vivo or have acquired such a phenotype in vivo, Actb-GFP Sca1$^+$ BM cells (FIG. 8B-$a$) were spiked at different concentrations in d7 islet-enriched fraction PDPC cultures (concurrent with PDPC appearance) derived from wild-type C57Bl/6 mice (n=6). During the ensuing week, GFP$^+$ cells began to proliferate and could be found throughout colonies of PDPC-like cells (FIG. 8A). On day 14, GFP$^+$CD45$^+$ cells were purified by FACS and analyzed by real-time qPCR (FIG. 8C). Freshly isolated Sca1$^+$ BM cells expressed low levels of CKs and Afp, which remained relatively constant following 7 days of culture in a PDPC culture environment and remained significantly lower than levels detected in PDPCs. Although levels of CK19 increased significantly (215-fold) by real-time RT-qPCR, this was only 15% of the level detected in CD45$^+$ PDPCs (FIG. 8C), demonstrating that the PDPC phenotype is not acquired ex vivo.

Discussion

Presented herein is a protocol by which a population of oval cell-like progenitor cells residing in the normal pancreas can be expanded and purified ex vivo. Unlike the previous descriptions for isolation of hepatic or pancreatic oval cells (Jeffers et al. 1996; Petersen et al. 2003; Petersen et al. 1998; Wang et al. 2003), pancreas-derived progenitor cells (PDPCs) can be generated in the absence of previous chemical injury or damage and can be expanded ex vivo.

PDPCs proliferate as round or oval-shaped cells and express many markers similar to mouse hepatic oval cells including AFP, cMet, CKs 7, 8, 18, 19, CD34, CD45, Sca1, and Thy1 (Knight et al 2005; Jeffers et al. 1996; Petersen et al. 2003; Petersen et al. 1998). Similar to oval cells, PDPCs produce numerous cytokines and growth factors including IL-6 and SCF, as determined by ELISA (data not shown) (Knight et al 2005; Fujio et al. 1996). Although CD45$^+$ PDPCs express the early endodermal marker AFP at levels much higher than a hepatic F2 oval cell-containing fraction, other epithelial markers are expressed at lower relative levels. The oval cell-containing fraction used in the studies described herein has been described as a size-purified (F2) primary cell fraction which appears during DDC-induced mouse liver oval cell activation (Wang et al. 2003). While PDPCs are uniformly CD45$^+$, some but not all cells within this population coexpress other stem cell markers including CD34, Sca1 and Thy1. Transcript levels for epithelial antigens in FACS selected CD45$^+$Sca$^+$ cells were significantly higher than in the total CD45$^+$ fraction and approached those measured in the F2 liver fraction. This data suggests that subpopulations of CD45$^+$ PDPCs may have a more early endoderm progenitor phenotype (Sca1$^{-/low}$, CK$^{low}$) whereas others may represent a more committed epithelial progenitor phenotype (Sca1$^+$, CK$^{high}$).

As PDPCs resemble oval cells, it was tested whether they could be induced towards a more mature endodermal fate. Similar to mouse pancreatic oval cells, exposure of PDPCs to HGF/scatter factor induced a marked change in morphology (Jeffers et al. 1996). While purified PDPCs tend to form colonies or clusters of round cells, HGF treatment induced a flattened, epithelioid morphology. In addition, 4-6 weeks following application of the hepatic differentiation conditions, occasional lumen-like structures could be detected (data not shown). Real-time RT-qPCR demonstrated that PDPCs acquired a more committed endodermal phenotype, expressing significantly higher levels of epithelial markers, endoderm transcription factors, and pancreatic transcription factors. Interestingly, as observed for cultured and primary mouse pancreatic oval cells, PDPCs began to express mature hepatic markers including Albumin even though they did not acquire a hepatocyte morphology (Ide et al. 1993). Immunohistochemistry confirmed that progeny of PDPCs with epithelioid morphology expressed Hnf3β.

While very few studies have evaluated pancreatic oval cells or their origin, many studies have investigated the origin of hepatic oval cells (Wang et al. 2003; Petersen et al. 1999; Menthena et al. 2004; Vig et al. 2006). Petersen et al. (1999)

suggested that, under certain pathological conditions, a bone marrow-derived cell may act as a liver (oval cell) progenitor. While other groups have reported similar results (Theise et al. 2000; Korbling et al. 2002), more recent data suggest the majority of oval cells arise from within the liver itself, with less than 1% of an exogenous BM origin (Wang et al. 2003; Menthena et al. 2004; Vig et al. 2006). In addition, a significant portion of the BM-derived cells were found to have fused with cells within the liver itself (Wang et al. 2003; Menthena et al. 2004). The inventors and others have demonstrated that cells can be cultured from rodent or human BM ex vivo and can subsequently be induced to a hepatic (Schwartz et al. 2002) or pancreatic (D'Ippolito et al. 2004) fate; however, it remains to be determined whether the long-term expansion endows the BM cells with this differentiation potential. In addition, recent work by Ruhnke et al (2005a; b) described the ability to differentiate short term ex vivo expanded human monocytes to hepatic and pancreatic fates. Using a series of lineage-tracing studies it was demonstrated herein that PDPCs do not originate from a pancreatic endodermal cell or a beta cell, but that PDPCs are derived from BM cells. Further characterization indicates that PDPCs are derived from the KSL-enriched hematopoietic stem cell fraction in BM. Although it cannot be excluded that only a small subpopulation of these cells contribute to PDPCs, it was demonstrated herein that PDPCs are derived from this stem cell enriched BM population. In addition, the data demonstrates that PDPCs are not the product of fusion between BM-derived cells and endodermal cells within the pancreas. Acquisition of the PDPC fate also does not appear to be imposed by coculture between hematopoietic cells and pancreatic cells ex vivo, as addition of Sca1$^+$ cells from BM to established PDPC cultures did not induce the endodermal phenotype seen in PDPCs. These results suggest that there exists a population of cells within the KSL fraction that has the potential to contribute to cells of non-hematopoietic lineages. As only 1:30 cells within the KSL population has been shown to possess long-term hematopoietic reconstitution potential (Osawa et al. 1996), the possibility exists that cells within this population have diverse potentials.

Current oval cell activation models in the rat (D-galactosamine (D-gal), retrosine/partial hepatectomy (Rs/PH), and 2-acetylaminofluorene/parital hepatectomy (2-AAF/PH)) or mouse (choline deficient, ethionine supplemented (CDE) diet or 3,5-diethoxycarbonyl-1,4-dihydro-collidine (DDC) diet) likely present a degree of damage repairable by endogenous epithelial stem/progenitor cells, without the need for a contribution from an exogenous source. As suggested by Knight et al. (2005), in the event that endogenous oval cells are exhausted, a BM population may serve as a last resort source. Ex vivo cultures likely present some of the signals required for the induction and proliferation of such exogenous oval cells.

Thus, PDPCs represent a novel, highly reproducible ex vivo expanded population of oval cell-like cells from an unmanipulated pancreas. PDPCs are believed to be derived from an exogenous bone marrow source and, like hepatic oval cells, coexpress hematopoietic and endodermal markers.

Bibliography

Brownlee, M., Nature, 2001. 414(6865):813-20.
Lechner & Habener, Am J Physiol Endocrinol Metab, 2003.284(2):E259-66.
Zulewski, H., et al., Diabetes, 2001. 50(3):521-33.
Cao et al., Immunity, 1995. 2:223-38.
Grossblatt N. Guide for Care and Use of Laboratory Animals: National Academy Press, 1996.
Ikuta and Weissman. Proc. Natl. Acad. Sci USA 1992. 89:1502-6.
Pipeleers, D. and Ling, Z. Diabetes Metab. Rev. 1992. 8:209-27.
Pociot, F. and McDermott, MF Genes Immun. 2002. 3:235-49.
Seaberg, R. M., et al., Nat Biotechnol, 2004. 22(9):1115-24.
Bonner-Weir, S., et al., Proc Natl Acad Sci USA, 2000. 97(14):7999-8004.
D'Amour, K. A., et al., Nat Biotechnol, 2005. 23(12):1534-41.
Yasunaga, M., et al., Nat Biotechnol, 2005. 23(12):1542-50.
Blyszczuk, P., et al., Int J Dev Biol, 2004. 48(10):1095-104.
Vaca, P., et al., Stem Cells, 2006. 24(2):258-65.
Dor, Y., et al., Nature, 2004. 429(6987):41-6.
Michalopoulos and DeFrances, Science, 1997. 276(5309): 60-6.
Oh, S. H., et al., Semin Cell Dev Biol, 2002. 13(6):405-9.
Knight, B., et al., Bioessays, 2005. 27(11):1192-202.
Ide, H., et al., Exp Cell Res, 1993. 209(1):38-44.
Jeffers, M., et al., Cell Growth Differ, 1996. 7(12):1805-13.
Petersen, B. E., et al., Hepatology, 2003. 37(3):632-40.
Petersen, B. E., et al., Hepatology, 1998. 27(2):433-45.
Guo, Z., et al., Transplantation, 2003. 75(7):909-15.
Gu, G., et al., Development, 2004. 131(1):165-79.
Wang, X., et al., Proc Natl Acad Sci USA, 2003. 100 Suppl 111881-8.
Schwartz, R. E., et al., J Clin Invest, 2002. 109(10):1291-302.
Schwartz, R. E., et al., Stem Cells Dev, 2005. 14(6):643-55.
Postic, C., et al., J Biol Chem, 1999. 274(1):305-15.
Gannon, M., et al., Genesis, 2000. 26(2): 143-4.
Novak, A., et al., Genesis, 2000. 28(3-4):147-55.
Petersen, B. E., et al., Science, 1999. 284(5417):1168-70.
Wang, X., et al., Nature, 2003. 422(6934):897-901.
Terada, N., et al., Nature, 2002. 416(6880):542-5.
Doyonnas, R., et al., Proc Natl Acad Sci USA, 2004. 101 (37):13507-12.
Fujio, K., et al., Exp Cell Res, 1996. 224(2):243-50.
Menthena, A., et al., Stem Cells, 2004. 22(6):1049-61.
Vig, P., et al., Hepatology, 2006. 43(2):316-24.
Theise, N. D., et al., Hepatology, 2000. 31(1):235-40.
Korbling, M., et al., N Engl J Med, 2002. 346(10):738-46.
D'Ippolito, G., et al., J Cell Sci, 2004. 117(Pt 14):2971-81.
Rao and Reddy, Methods in Cell Science, Volume 13, Number 2/June, 1991, 121-124.
Ruhnke, M., et al., Transplantation, 2005a. 79(9):1097-103.
Ruhnke, M., et al., Gastroenterology, 2005b. 128(7):1774-86.
Osawa, M., et al., J Immunol, 1996. 156(9):3207-14.
Jayawickreme and Kost, Curr. Opin. Biotechnol. 1997. 8:629-634.
Leffert, H. L., et al., In: *The Liver: Biology and Pathobiology* (Arias, I., et al., eds.), 2$^{nd}$ ed., Raven, New York, 1988. pp. 833-850.
Lim, J. W., and Bodnar, A. Proteomics, 2002. 2(9):1187-203.
Rice, J. W., et al., Anal. Biochem., 1996. 241:254-259.
Suzuki, A., et al., Transplant. Proc., 2000. 32:2328-2330.

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. A method of obtaining endodermal progenitor cells comprising:

(a) culturing a cell population obtained from an adult endodermal tissue to induce cluster formation in culture medium;

(b) seeding the clusters in a vessel coated with one or more attachment factors, wherein cells comprising the clusters adhere to the one or more attachment factors and form a monolayer;

(c) culturing the monolayer clusters in culture medium until a population of endodermal progenitor cells emerges; and (d) isolating the endodermal progenitor cells, wherein the isolated endodermal progenitor cells do not express smooth muscle actin or PDX-1, wherein a function of a cell in the tissue is not reduced by application of an exogenous stressor prior to harvesting the tissue, wherein the exogenous stressor is adverse chemicals, nutritional stressors, cell depletion or physical stress.

2. The method of claim 1, wherein the tissue is derived from liver, stomach, intestine, pancreas, lung, colon, bladder or thyroid.

3. The method of claim 1, wherein the tissue is pancreas.

4. The method of claim 1, wherein the clusters areisolated prior to culturing in step (b).

5. The method of claim 1, wherein the one or more attachment factors comprise one or more of collagen type I, collagen type II, collagen type IV, fibronectin, chondroitin sulfate, vitronectin, thrombospondin or matrigel.

6. The method of claim 1, wherein the culture medium of step (b) is changed every two to three days for at least about 7 days.

7. The method of claim 6, wherein after about 7 days the culture medium of step (b) is not changed prior to isolating the endodermal progenitor cells.

8. The method of claim 1, wherein the culture medium of step (a) and/or (b) comprises serum.

9. The method of claim 8, wherein the serum content is about 0.5% to about 5%.

10. The method of claim 1, wherein the culture media of step (a) and/or (b) comprises one or more of epidermal growth factor (EGF), leukemia inhibitory factor (LIP), platelet-derived growth factor (PDGF), or basic fibroblast growth factor (bFGF).

11. The method of claim 1, wherein the cell population is subjected to continuous density gradient centrifugation prior to step (a).

12. The method of claim 1, wherein the tissue is disassociated prior to step (a).

13. The method of claim 12, wherein the tissue is disassociated enzymatically.

14. The method of claim 13, wherein the enzyme comprises one or more of collagenase, trypsin, dispase I, hyaluronidase, therinolysin, neutral protease, liberase RI, DNase I, pancreatin, or pronase.

15. The method of claim 1, where n the tissue is obtained from a mammal.

16. The method of claim 15, wherein the mammal is a human, swine, mouse or rat.

17. The method of claim 1 further comprising differentiating the endodermal progenitor cells to yield an endodermal cell type.

18. The method of claim 17, wherein the differentiated endodermal cull type is selected from the mono consisting of pancreatic, islet, intestinal, thyroid, lung, colon, bladder and liver cell types.

19. The method of claim 17, wherein the endodermal progenitor cells are differentiated in the presence of one or more differentiation factors comprising β-cellulin, glucagon-like peptide-1 (GLP-1), hepatocyte growth factor (HGF), fibroblast growth factor (FGF), epidermal growth factor (EGF), keratinocyte growth factor (KGF), nicotinamide, transforming growth factor-α(TGF-α), transforming growth factor-β (TGF-β), activin, cyclopamin, bone morphogenetic protein 4 (BMP4), sonic hedgehog (SHH) antibody, Oncostatin M, dexamethasone, exendin4, growth differentiation factor 11 (GDF11) or a combination thereof.

* * * * *

UNITED STATES PATENT AND TRADEMARK OFFICE
CERTIFICATE OF CORRECTION

PATENT NO. : 9,005,964 B2  
APPLICATION NO. : 12/312731  
DATED : April 14, 2015  
INVENTOR(S) : Verfaillie et al.

Page 1 of 2

It is certified that error appears in the above-identified patent and that said Letters Patent is hereby corrected as shown below:

On Title page 3, in column 1, under "Other Publications", line 29, delete "populationof" and insert --population of--, therefor In the Specification In column 1, line 15-18, delete "This invention was made with the assistance of government support under United States Grant Nos. R01-HL073221 and U19 DK61244 from the National Institutes of Health. The government may have certain rights in the invention." and insert --This invention was made with government support under HL073221 and DK061244 awarded by the National Institutes of Health. The government has certain rights in the invention.--, therefor In the Claims In column 58, line 65, in Claim 1, after "monolayer", delete "clusters", therefor In column 59, line 3, in Claim 1, delete "PDX-1," and insert --Pdx-1,--, therefor In column 59, line 13, in Claim 4, delete "areisolated" and insert --are isolated--, therefor In column 59, line 31, in Claim 10, delete "(LIP)," and insert --(LIF),--, therefor In column 59, line 31-32, in Claim 10, delete "platelet-derived" and insert --platelet derived--, therefor In column 60, line 10, in Claim 14, delete "therinolysin," and insert --thermolysin,--, therefor In column 60, line 12, in Claim 15, delete "where n" and insert --wherein--, therefor Signed and Sealed this  
Eighth Day of September, 2015

Michelle K. Lee  
*Director of the United States Patent and Trademark Office*

CERTIFICATE OF CORRECTION (continued)
U.S. Pat. No. 9,005,964 B2

In column 60, line 20, in Claim 18, delete "cull" and insert --cell--, therefor

In column 60, line 20, in Claim 18, delete "mono" and insert --group--, therefor